(12) United States Patent
O'Connor et al.

(10) Patent No.: US 7,074,327 B2
(45) Date of Patent: Jul. 11, 2006

(54) SAMPLE PREPARATION FOR PARALLEL CHROMATOGRAPHY

(75) Inventors: Stephen D. O'Connor, Pasadena, CA (US); Eugene Dantsker, Sierra Madre, CA (US); Christoph D. Karp, Pasadena, CA (US); Mike S. Lee, Newtown, PA (US); Surekha Vajjhala, Los Angeles, CA (US)

(73) Assignee: Nanostream, Inc., Pasadena, CA (US)

(*) Notice: Subject to any disclaimer, the term of this patent is extended or adjusted under 35 U.S.C. 154(b) by 166 days.

(21) Appl. No.: 10/841,242

(22) Filed: May 7, 2004

(65) Prior Publication Data
US 2004/0226884 A1 Nov. 18, 2004

Related U.S. Application Data

(60) Provisional application No. 60/469,476, filed on May 8, 2003.

(51) Int. Cl.
*B01D 15/08* (2006.01)

(52) U.S. Cl. .................. 210/198.2; 210/656; 210/143; 422/70; 422/100; 422/101

(58) Field of Classification Search ............... 210/635, 210/656, 198.2, 143, 659, 502.1; 422/70, 422/100, 101
See application file for complete search history.

(56) References Cited

U.S. PATENT DOCUMENTS

| | | | |
|---|---|---|---|
| 4,946,795 A | 8/1990 | Gibbons et al. | 436/179 |
| 5,030,418 A | 7/1991 | Miyata | 422/63 |
| 5,478,751 A | 12/1995 | Oosta et al. | 436/165 |
| 5,658,413 A | 8/1997 | Kaltenbach et al. | 156/272.8 |
| 5,690,763 A | 11/1997 | Ashmead et al. | 156/60 |
| 5,731,212 A | 3/1998 | Gavin et al. | 436/526 |
| 5,783,450 A | 7/1998 | Yoshida et al. | 436/161 |
| 5,824,204 A * | 10/1998 | Jerman | 204/601 |
| 5,839,467 A | 11/1998 | Saaski et al. | 137/501 |
| 5,863,502 A | 1/1999 | Southgate et al. | 422/58 |
| 5,872,010 A | 2/1999 | Karger et al. | 436/173 |
| 5,928,880 A | 7/1999 | Wilding et al. | 435/7.21 |
| 6,004,450 A | 12/1999 | Northrup et al. | 205/656 |

(Continued)

FOREIGN PATENT DOCUMENTS

EP 0 545 284 A1 6/1993

(Continued)

OTHER PUBLICATIONS

*Development of a high-pressure gradient pumping system for parrallel liquid chromatography/mass spectrometry for the analysis of combinatorial libaries*, "Rapid Communications in Mass Spectrometry," 2001, 15, 1244-1249, Letter to the Editor, John Wiley & Sons, Ltd.

(Continued)

*Primary Examiner*—Ernest G. Therkorn
(74) *Attorney, Agent, or Firm*—Vincent K. Gustafson; Intellectual Property/Technology Law

(57) ABSTRACT

Systems and methods are provided for preparing samples for chromatographic separations and then chromatographically separating the prepared samples, preferably in a high-throughput fashion utilizing multiple parallel first (fluid) processing regions in fluid communication with multiple parallel second (fluid) processing regions wherein the each second processing region includes a chromatography column. One or more common fluid supplies may be utilized in each of the sample preparation and separation steps to minimize the number of requisite fluid connections and external components such as pumps, reservoirs, pulse dampers, flow controllers, and the like.

25 Claims, 24 Drawing Sheets

U.S. PATENT DOCUMENTS

| | | | |
|---|---|---|---|
| 6,043,080 A | 3/2000 | Lipshutz et al. | 435/287.2 |
| 6,063,283 A | 5/2000 | Shirota et al. | 210/656 |
| 6,117,396 A | 9/2000 | Demers | 422/100 |
| 6,240,790 B1 | 6/2001 | Swedberg et al. | 73/863.21 |
| 6,296,771 B1 | 10/2001 | Miroslav | 210/656 |
| 6,312,888 B1 | 11/2001 | Wong et al. | 435/4 |
| 6,331,439 B1 | 12/2001 | Cherukuri et al. | 436/174 |
| 6,408,878 B1 | 6/2002 | Unger et al. | 137/597 |
| 6,416,716 B1 | 7/2002 | Shukla et al. | 422/101 |
| 6,436,292 B1 | 8/2002 | Petro | 210/656 |
| 6,437,345 B1 | 8/2002 | Bruno-Raimondi et al. | 250/458.1 |
| 6,458,273 B1 | 10/2002 | Krakover et al. | 210/198.2 |
| 6,461,515 B1 | 10/2002 | Safir et al. | 210/656 |
| 6,485,690 B1 | 11/2002 | Pfost et al. | 422/102 |
| 6,494,614 B1 | 12/2002 | Bennett et al. | 366/336 |
| 6,532,978 B1 | 3/2003 | Müller-Kuhrt et al. | 137/1 |
| 6,581,441 B1 | 6/2003 | Paul | 73/61.52 |
| 6,585,939 B1 | 7/2003 | Dapprich | 422/99 |
| 6,603,546 B1 | 8/2003 | Barbieri et al. | 356/318 |
| 6,613,581 B1 | 9/2003 | Wada et al. | 436/518 |
| 6,635,226 B1 | 10/2003 | Tso et al. | 422/129 |
| 6,637,463 B1 | 10/2003 | Lei et al. | 137/803 |
| 6,664,104 B1 | 12/2003 | Pourahmadi et al. | 435/288.6 |
| 6,812,030 B1 | 11/2004 | Ozbal et al. | 436/50 |
| 6,936,167 B1* | 8/2005 | Hobbs et al. | 210/198.2 |
| 2001/0013494 A1 | 8/2001 | Maiefski et al. | 210/656 |
| 2002/0033337 A1 | 3/2002 | Ausserer et al. | 204/453 |
| 2002/0048536 A1 | 4/2002 | Bergh et al. | 422/130 |
| 2002/0068357 A1 | 6/2002 | Mathies et al. | 435/287.2 |
| 2002/0068366 A1 | 6/2002 | LaDine et al. | 436/518 |
| 2002/0158022 A1 | 10/2002 | Huang et al. | 210/656 |
| 2002/0199094 A1 | 12/2002 | Strand et al. | 713/150 |
| 2003/0094415 A1 | 5/2003 | Tanimura | 210/656 |
| 2003/0118486 A1 | 6/2003 | Zhou et al. | 422/102 |
| 2003/0150792 A1* | 8/2003 | Koehler et al. | 210/321.84 |
| 2003/0150806 A1* | 8/2003 | Hobbs et al. | 210/635 |
| 2003/0162304 A1 | 8/2003 | Dority et al. | 436/180 |
| 2003/0200794 A1 | 10/2003 | Paul | 73/54.05 |
| 2003/0230524 A1 | 12/2003 | Soga et al. | 210/198.2 |
| 2004/0158433 A1 | 8/2004 | Wimschneider et al. | 702/183 |
| 2005/0048669 A1* | 3/2005 | Hobbs et al. | 436/180 |

FOREIGN PATENT DOCUMENTS

| | | |
|---|---|---|
| EP | 0 686 848 A1 | 12/1995 |
| WO | WO 98/04909 | 2/1998 |
| WO | WO 98/35376 | 8/1998 |
| WO | WO 00/51720 A3 | 9/2000 |
| WO | WO 00/72970 A1 | 12/2000 |
| WO | WO 00/76662 A2 | 12/2000 |
| WO | WO 01/09598 A1 | 2/2001 |
| WO | WO 01/32930 A1 | 5/2001 |
| WO | WO 02/22250 A2 | 3/2002 |
| WO | WO 02/29106 A2 | 4/2002 |
| WO | WO 02/056006 A2 | 7/2002 |
| WO | WO 03/002226 A1 | 1/2003 |

OTHER PUBLICATIONS

Fang, Liling et al., *High-throughput liquid chromatograpohy Ultraviolet.mass spectrometric analysis of combinatorial libraries using an eight-channel multiplexed electrospray time-of-flight mass spectrometer*, "Rapid Communications in Mass Spectrometry," 2002; 16:1440-1447.

Manica, Drew P. et al., "Dual Electrochemical and Optical Detection on a Microfabricated Electrophoresis Chip," *Micro Total Analysis Systems*, J.M. Ramsey and A. van den Berg (eds.), 2001, Kluwer Academic Publishers, the Netherlands, pp. 262-264.

Zweigenbaum, Jerry et al., *High-Throughput Bioanalytical LC/MS/MS Determination of Benzodiazepines in Human Urine: 1000 Samples per 12 Hours*, "Analytical Chemistry," vol. 71, No. 13, Jul. 1, 1999, pp. 2294-2300.

Jacobson, S.C. et al., "Micro-Scale Liquid Phase Sensors: Chromatography on a Chip," Abstracts of Papers, Part 1, American Chemical Society, 207th ACS National Meeting, Mar. 13-17, 1994, San Diego, CA.

Broyles, Scott B. et al., "Sample Concentration and Separation on Microchips," *Micro Total Analysis Systems*, J.M. Ramsey and A. van den Berg (eds.), 2001, Kluwer Academic Publishers, the Netherlands, pp. 537-538.

Wagner, Knut et al., *An Automated On-Line Multidimensional HPLC System for Protein and Peptide Mapping with Integrated Sample Preparation*, "Analytical Chemistry," vol. 74, No. 4, Feb. 15, 2002, pp. 809-820.

Berna, M. et al., *Collection Storage, and Filtration of in Vivo Study Samples Using 96-Well Filter Plates To Facilitate Automated Sample Preparation and LC/MS.MS Analysis*, "Analytical Chemistry," vol. 74, No. 5, Mar. 1, 2002, pp. 1197-1201.

Grodzinski, Piotr Dr., "Development of Plastic Microfluidic Devices for Sample Preparation," BioMEMS 2000, Presentation, Columbus, Ohio, Sep. 24, 2000, Motorola Labs.

Taylor, M.T. et al., "Fully Automated Sample Preparation for Pathogen Detection Performed in a Microfludic Cassette," *Micro Total Analysis Systems*, J.M. Ramsey and A. van den Berg (eds.), 2001, pp. 670-672, Kluwer Academic Publishers, The Netherlands.

Sjölander, Stefan et al., *Integrated Fluid Handling System for Biomolecular Interaction Analysis*, "Analytical Chemistry," vol. 63, No. 20, Oct. 15, 1991, pp. 2338-2345, Palm, Anders et al., "Integrated Sample Preparation and MALDI MS on a disc," *Micro Total Analysis Systems*, J.M. Ramsey and A, van den Berg (eds.), 2001, pp. 216-218, Kluwer Academic Publishers, The Netherlands.

Khandurina, Julia et al., *Micropreparative Fraction Collection in Microfluidic Devices*, "Analytical Chemistry," vol. 74, No. 7, Apr. 1, 2002, pp. 1737-1740.

Wang, Xuan-Qi et al., "Polymer-Based Electrospray Chips for Mass Spectrometry," 1997, California Institute of Technology, Pasadena, CA. [publication source unknown]/

Yin, Hongfeng et al., "A polymeric microfluidic device with integrated mass-spectrometer interface," 2002, Aligent Laboratories, Palo Alto, CA [publication source unknown].

Kuwano, Hiroki et al., "Research and Development of Microsystems," 1996, NTT Integrated Information & Energy Systems Laboratories.

Shediac, Renée et al., *Reversed-phase electrochromatography of amino acids and peptides using porous polymer monoliths*, "Journal of Chromatography A," 925 (2001) 251-263, Elsevier Science B.V.

Bochner, BR, *Sleuthing Out Bacterial Identities*, "Nature," 1989, vol.: No. 6220, pp. 157-158.

Lesney. Mark S. et al., *Solid-Phase Attraction*, "Today's Chemist at Work," Feb. 2002, American Chemical Society, pp. 46-50.

Tan, Aimin et al., *Chip-Based-Phase Extraction Pretreatment for Direct Electrospray Mass Spectrometry Analyis Using an Array of Monolithic Columns in a Polymeric Substrate*, "Analytical Chemistry," vol. 75, No. 20 Oct. 15, 2003, pp. 5504-5511.

Sato Kiichi et al., "Integrated Immunoassay System Using Multichannel Microchip for Simultaneous Determination," *Micro Total Analysis Systems*, J.M. Ramsey and A. van den Berg (eds.), 2001, 511-512, Kluwer Acedemic Publishers, The Netherlands.

Norris, Ann M. et al., "Silicone Materials for Chip-Scale Packaging," Mar. 1998, www.chipscalereview.com/9803/smaterials1.htm.

Baryla, Nicole E. et al., *Simultaneous Separation of Cationic and Anionic Proteins Using Zwitterionic Surfactants in Capillary Electrophoresis*, "Analytical Chemistry," vol. 72, No. 10, May 15, 2000, pp. 2280-2284.

Verpoorte Elisabeth M.J. et al., *Three-dimensional micro flow manifolds for miniaturized chemical analysis systems*, "J, Micromech. Microeng.," 4(1994) 246-256, Printed in the UK.

"HPLC PAL Systems—Front End Automation Systems for Liquid Chromatography," Brochure, CTC Analytics AG, Zwingen, Switzerland [publication date unknown].

Jang, Ling-Sheng et al., *Transport of Particle-Laden Fluids Through Fixed Valve Micropumps*, "Microelectromechanical Systems (MEMS)", vol. 1, 1999.

Majors, Ronald E., *Trends in Sample Preparation*, "LCGC North America," vol. 20, No. 12, Dec. 2002.

Willis, Randall C., *Preparing for Proteins*, "Today's Chemist at Work," Mar. 2004, pp. 34-38.

\* cited by examiner

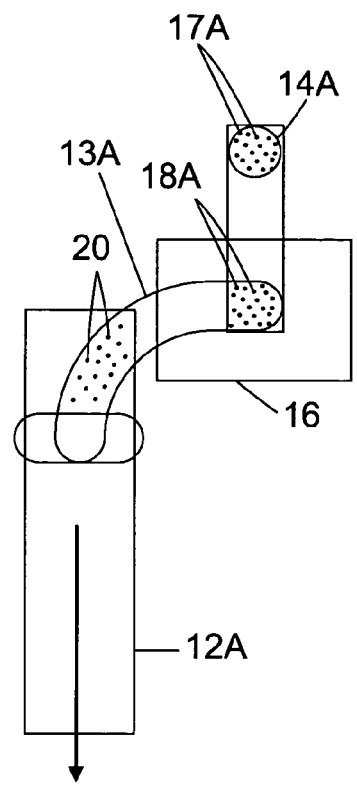
FIG._1B
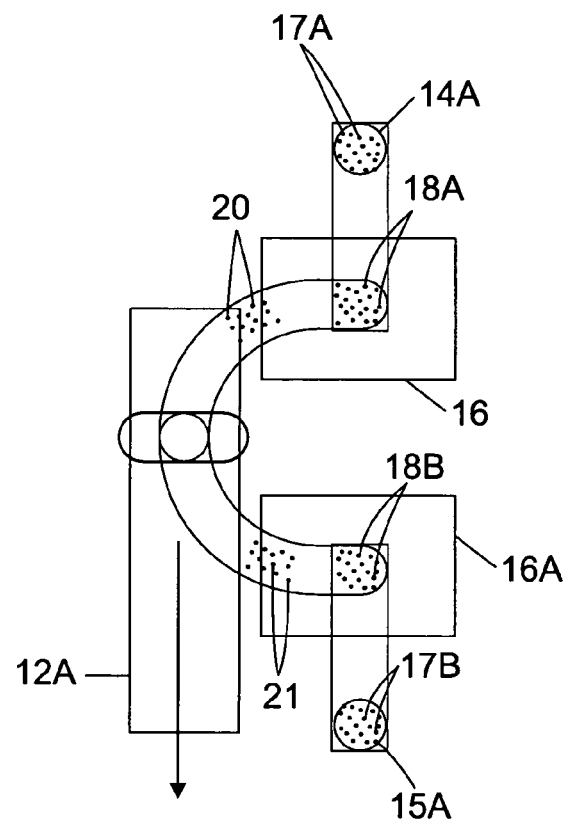
FIG._2
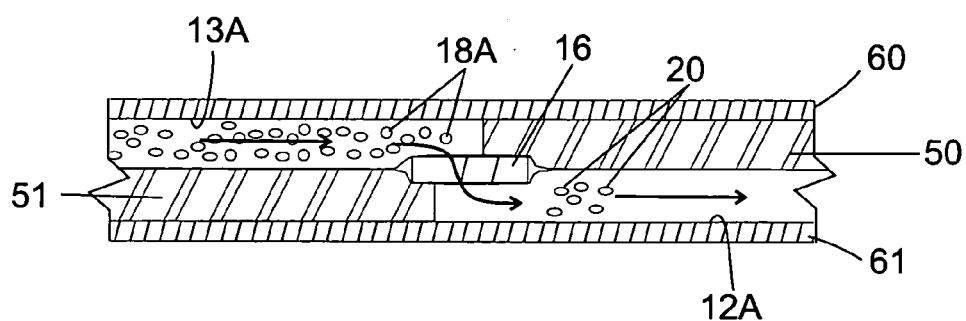
FIG._1C

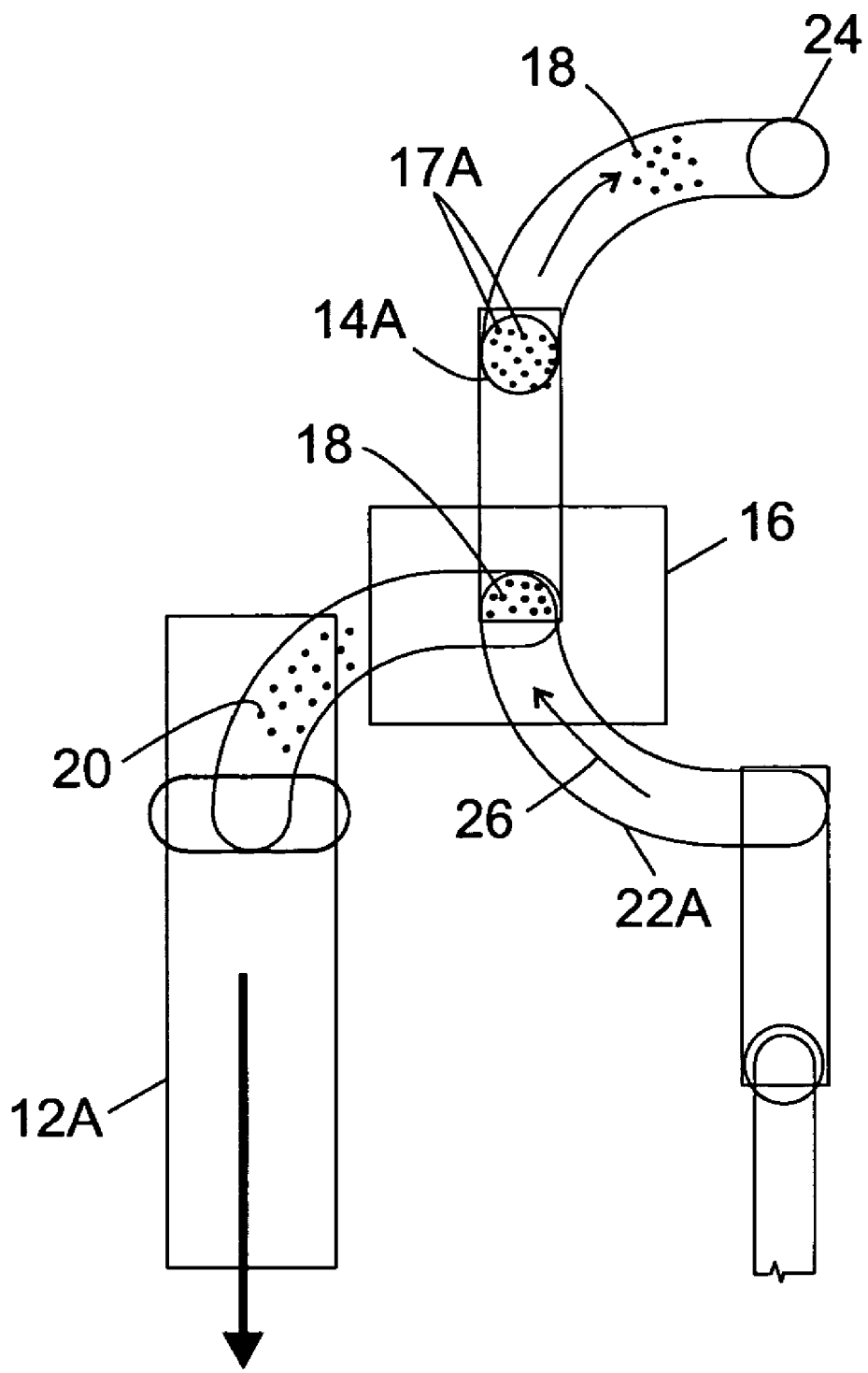
FIG._3

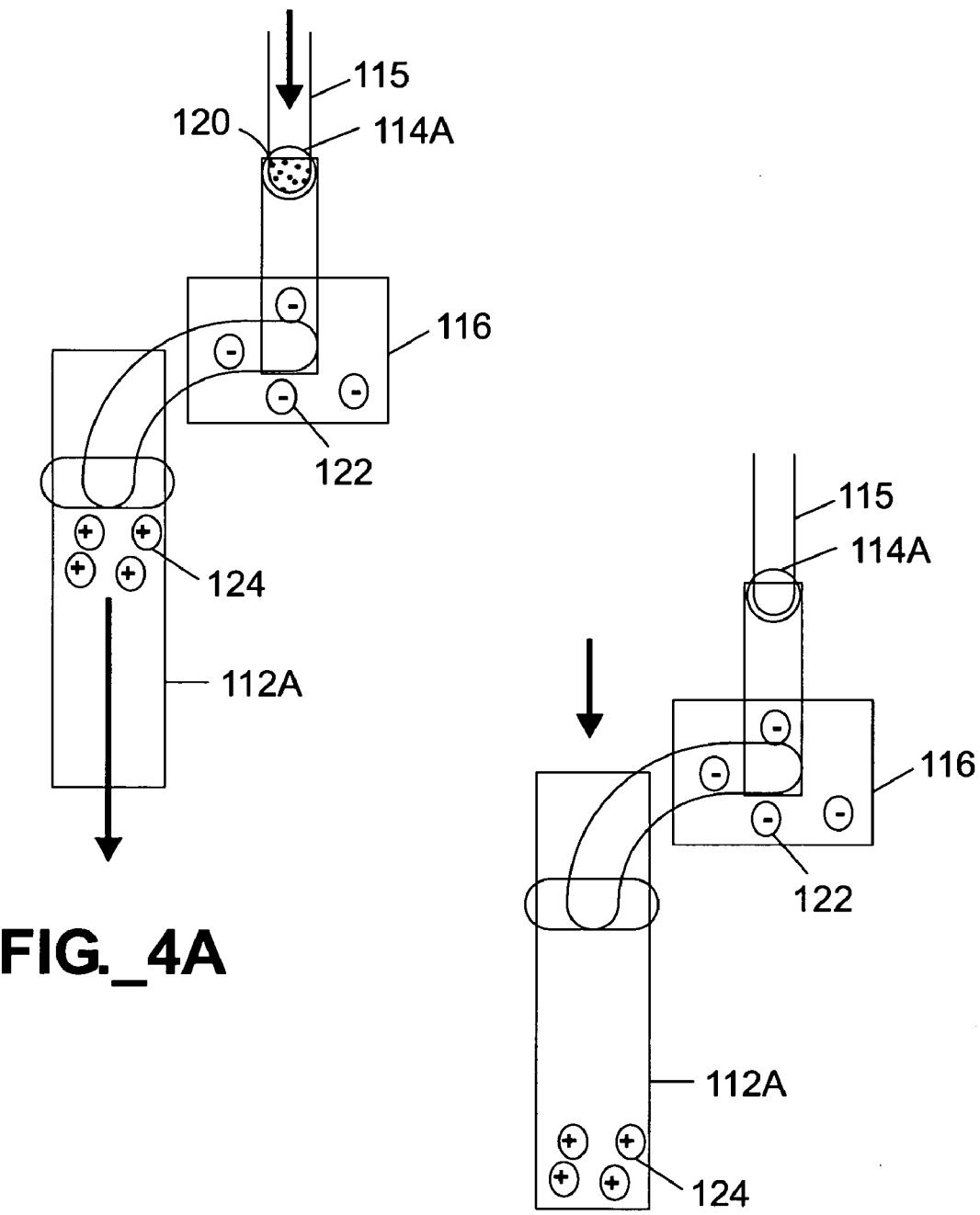

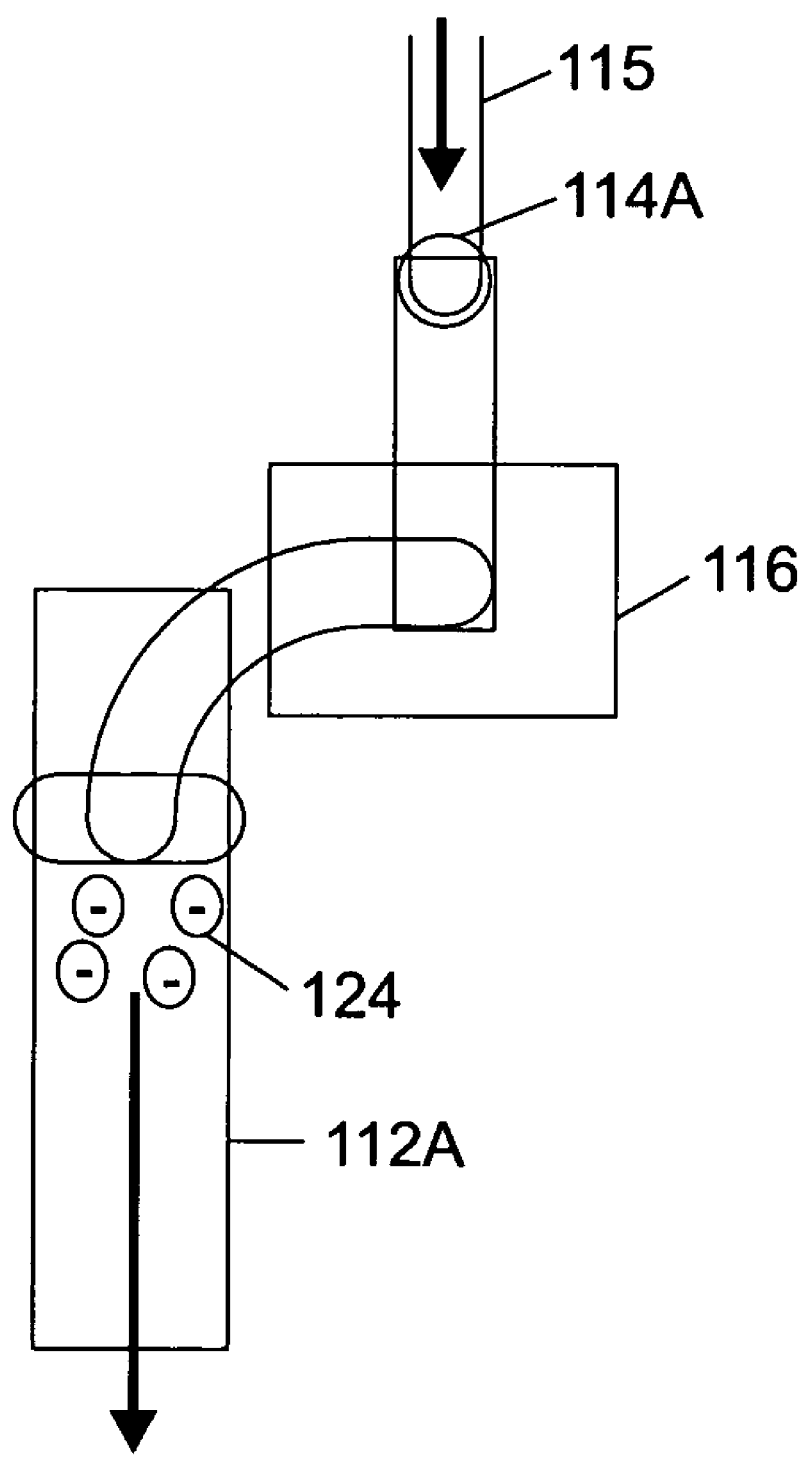
FIG._4C

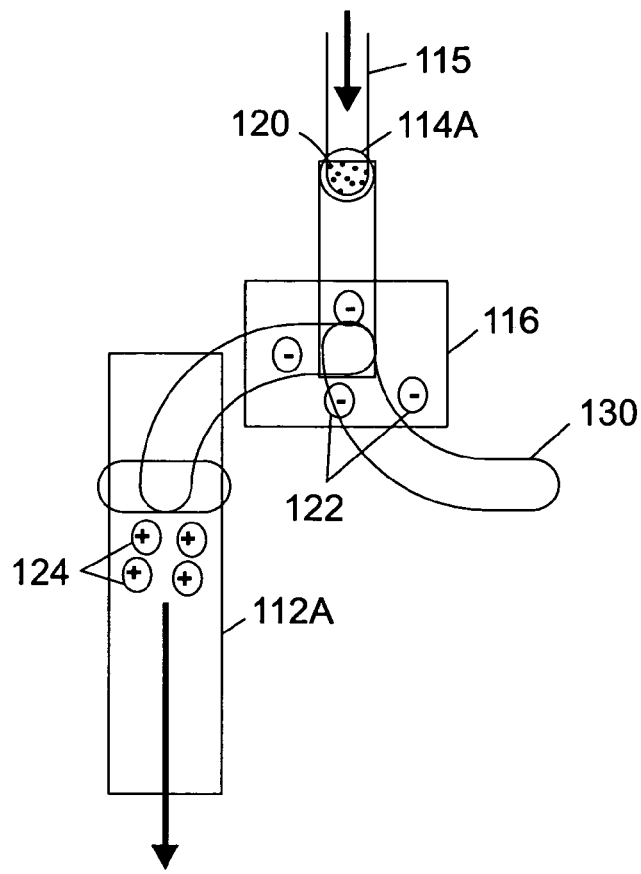
FIG._5A
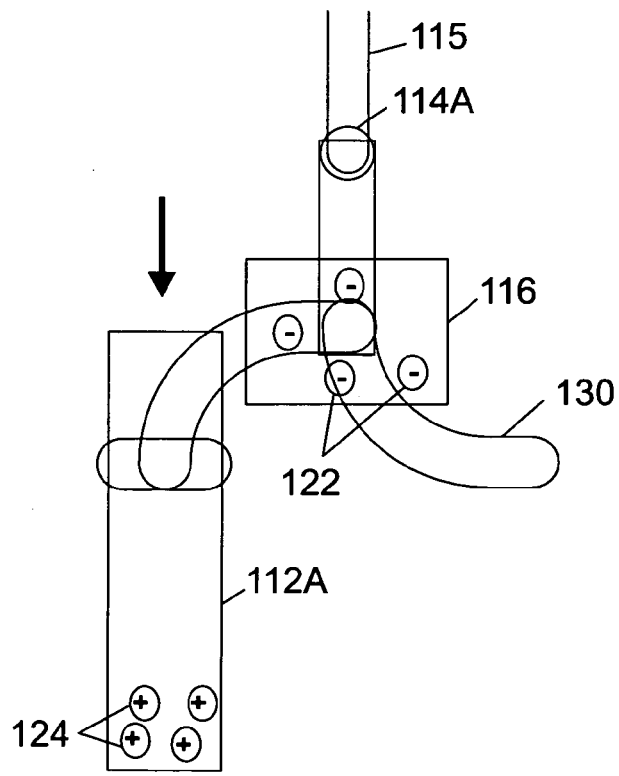
FIG._5B

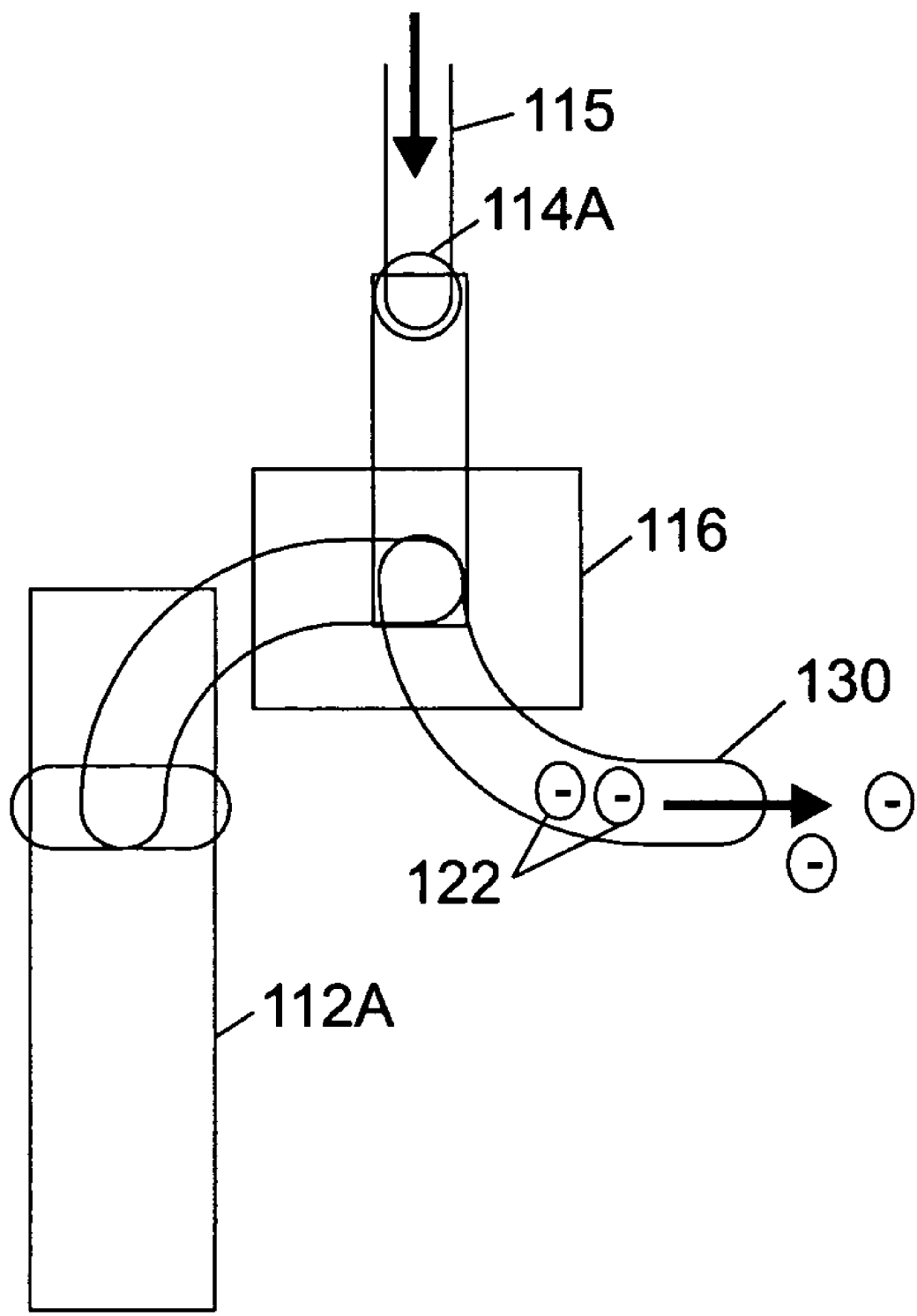
FIG._5C

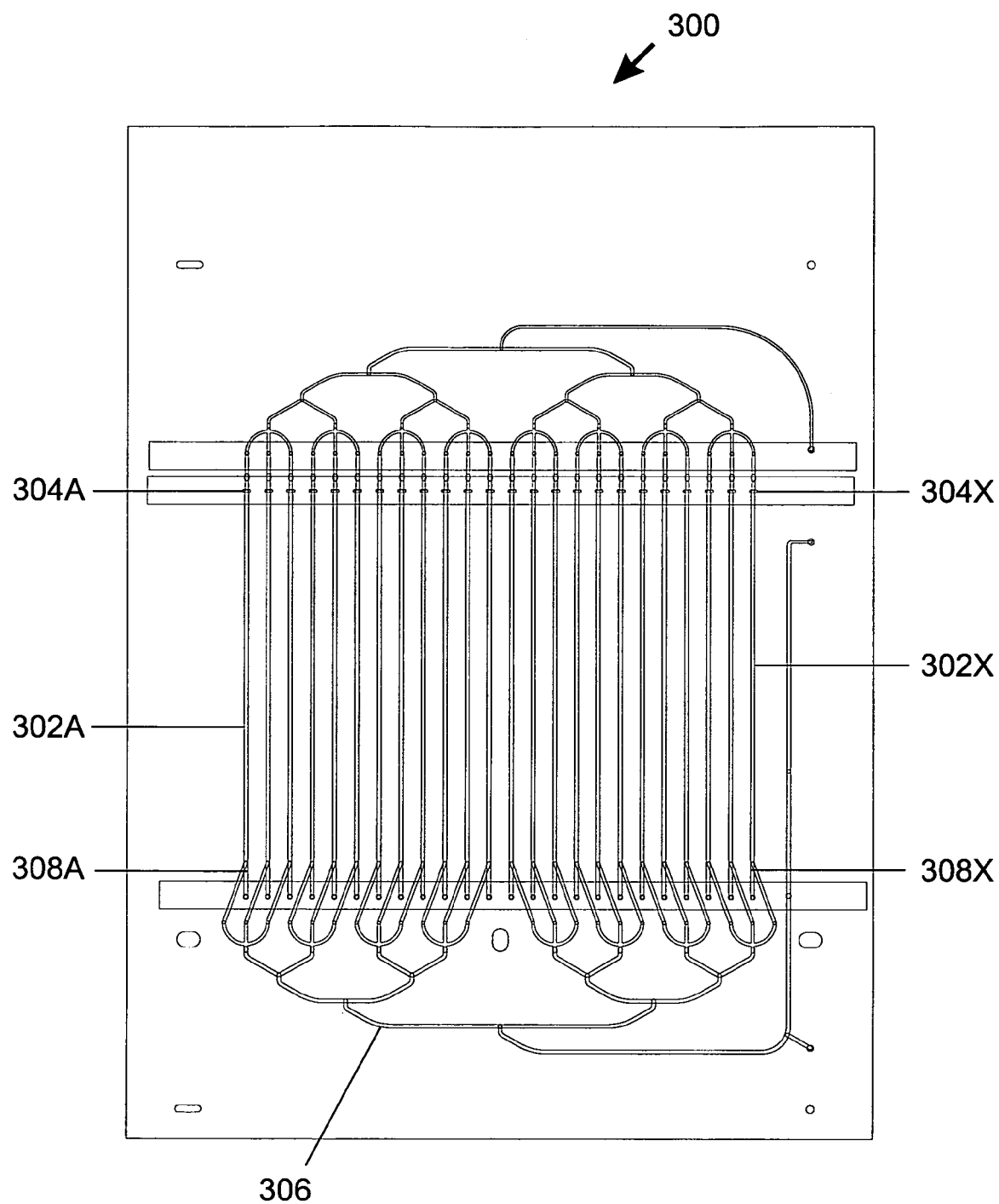
FIG._6

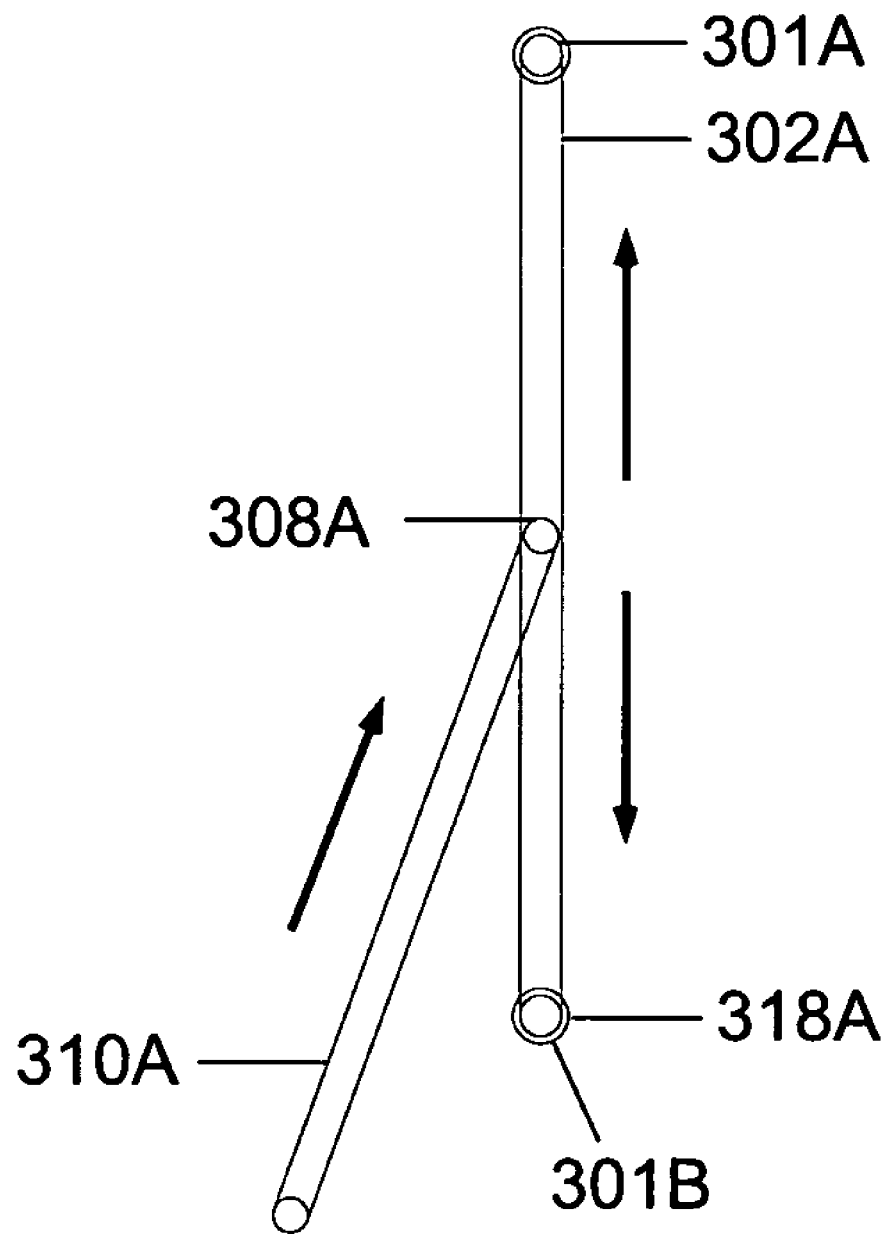
FIG._7A

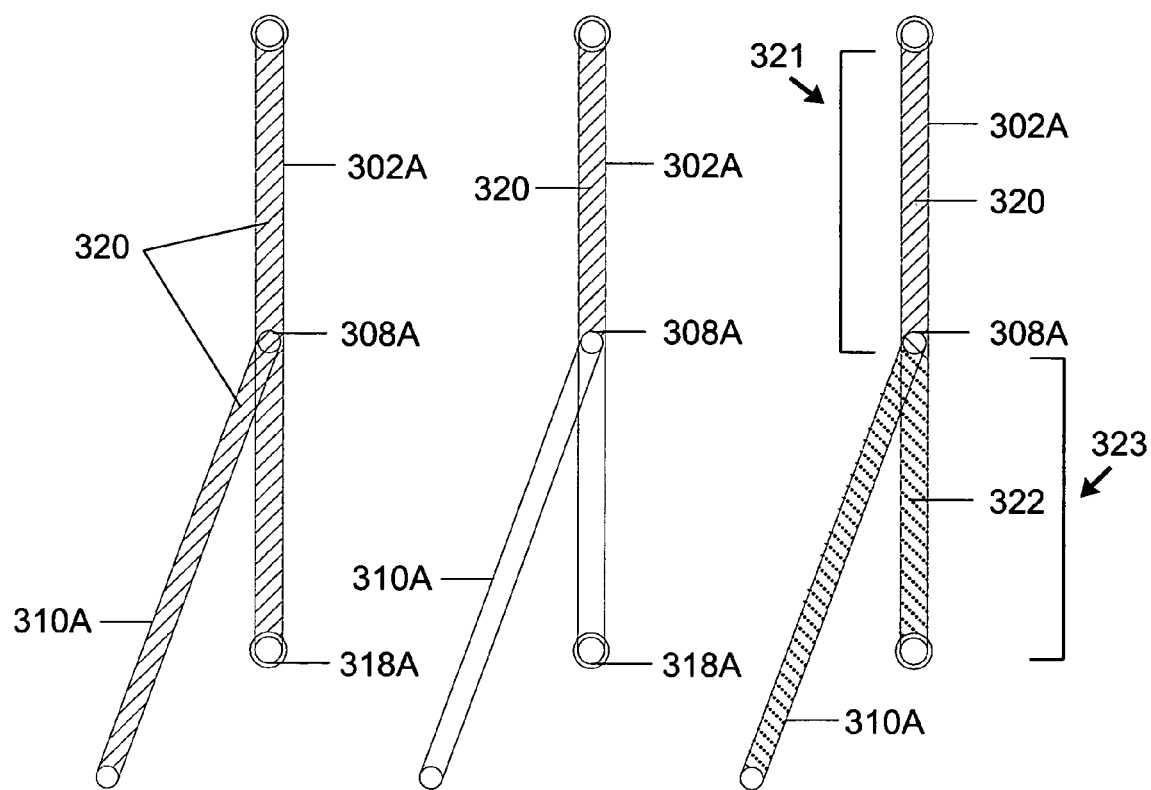
FIG._7B   FIG._7C   FIG._7D

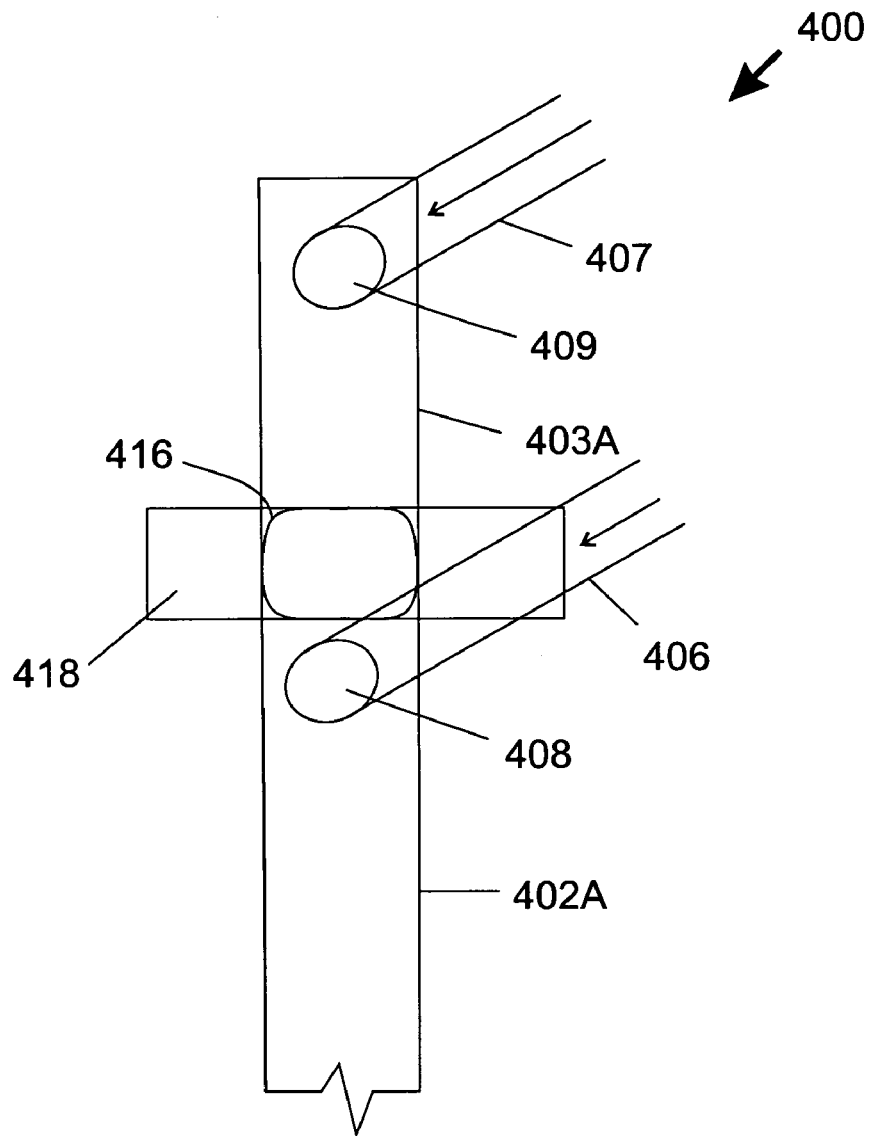
FIG._8A
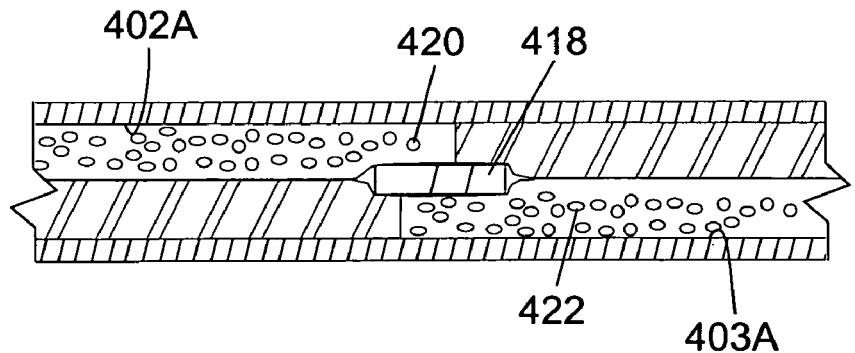
FIG._8B

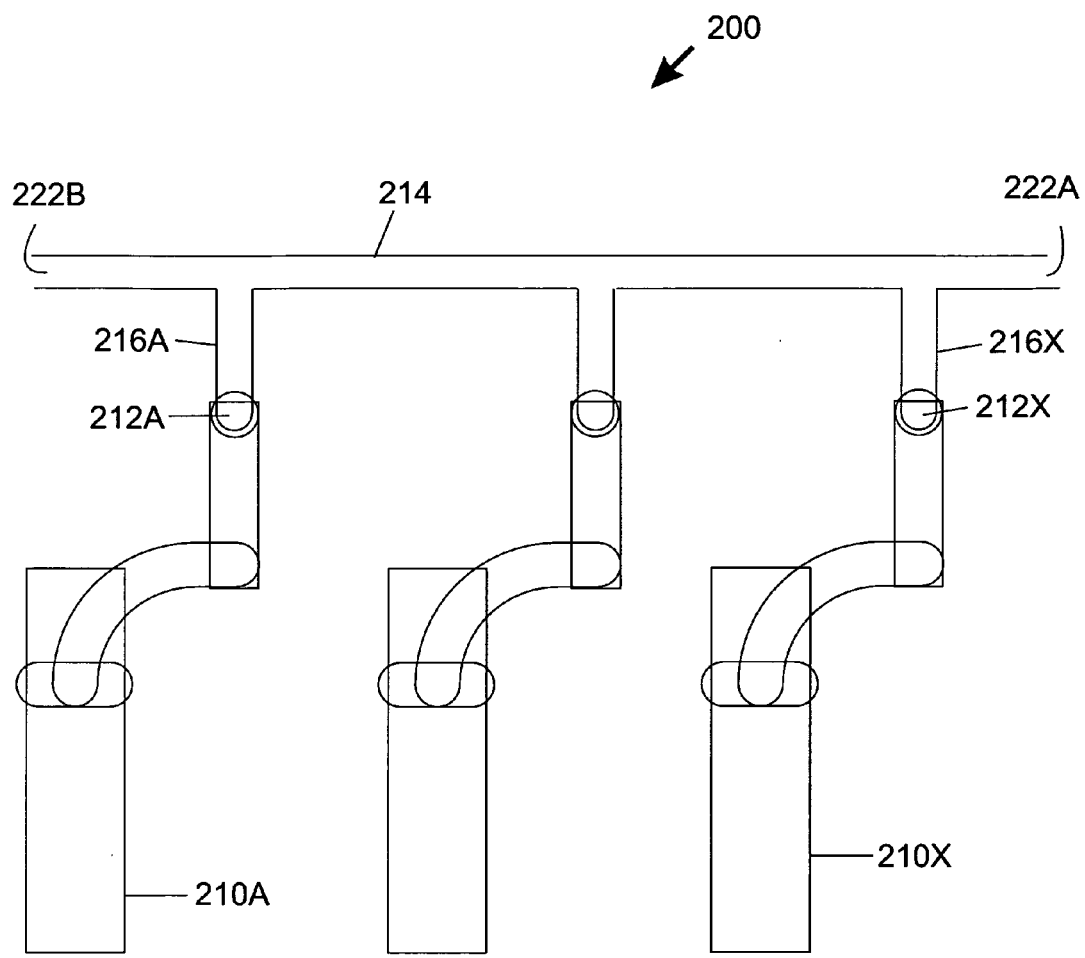
FIG._9A

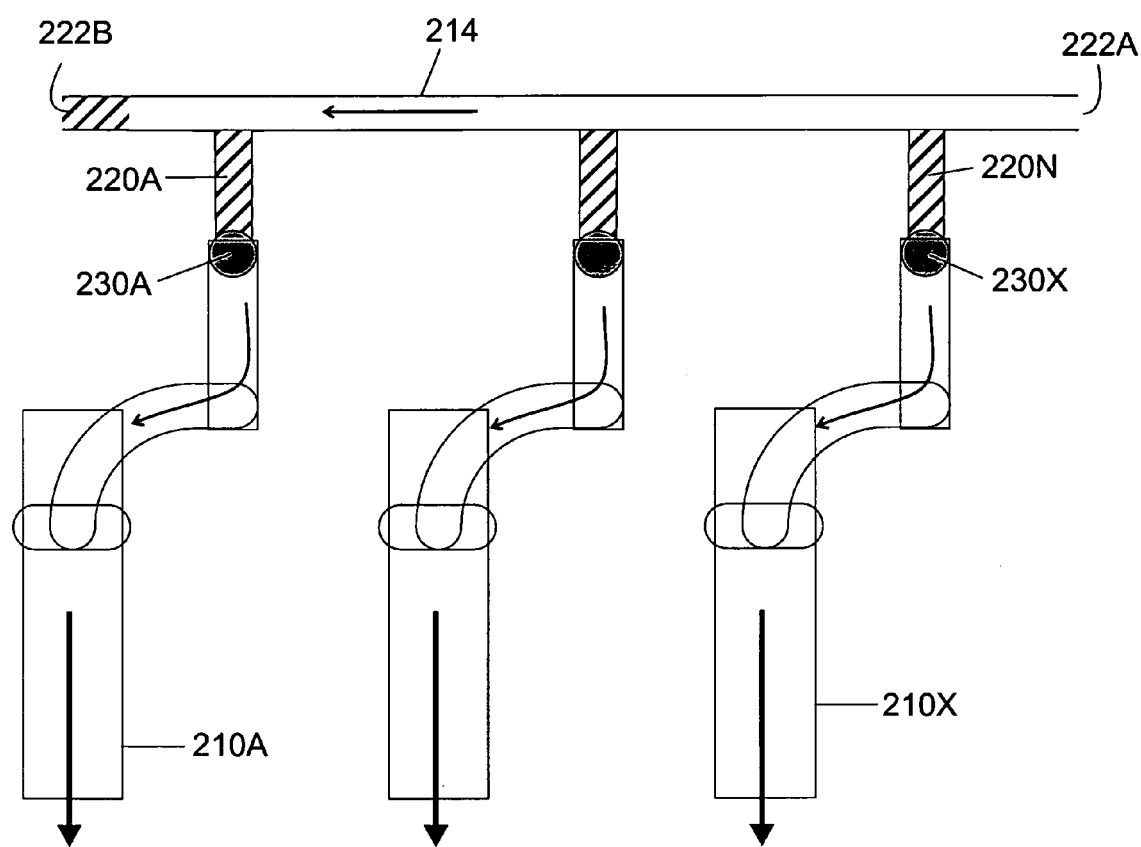
FIG._9C

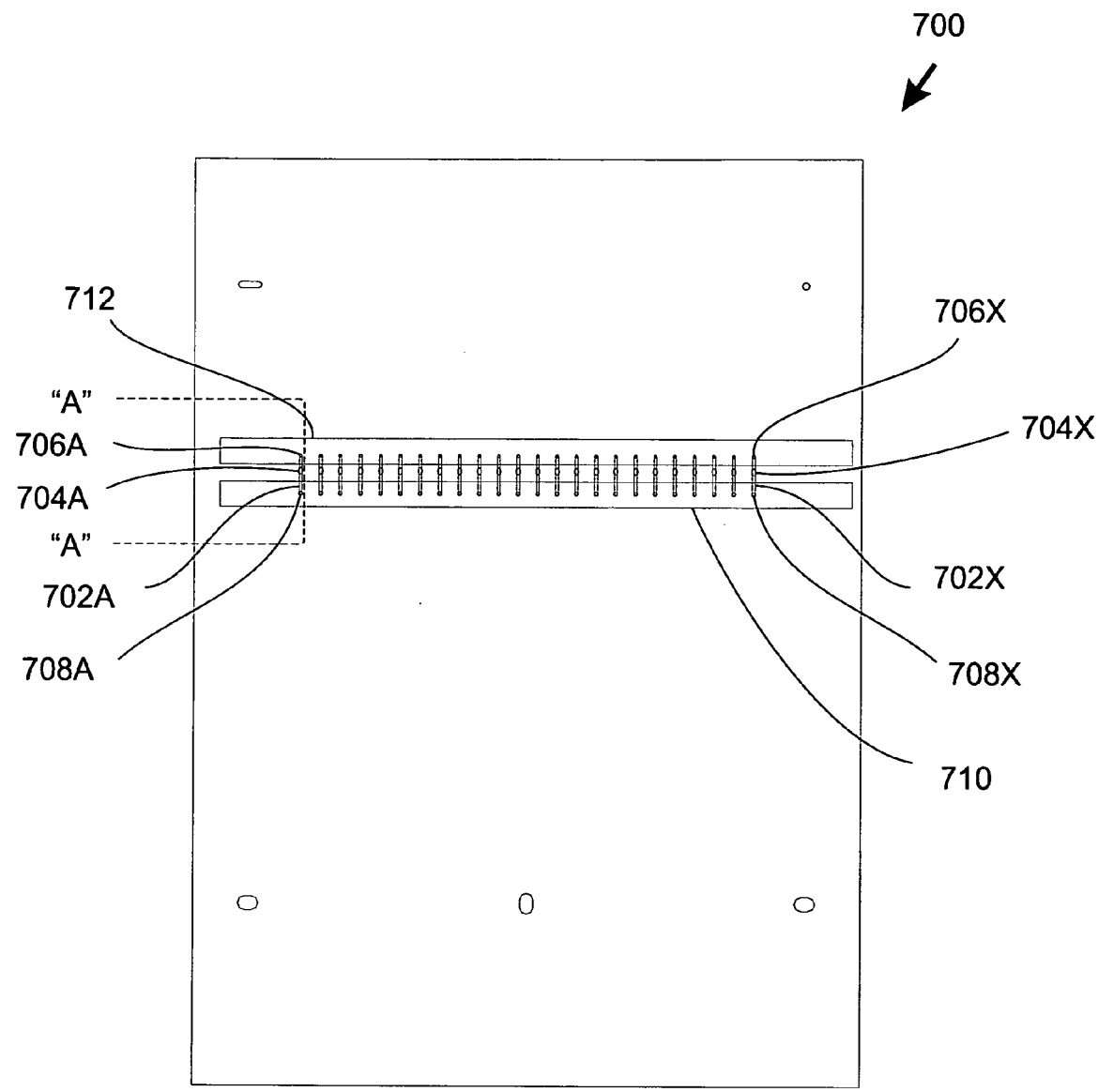
FIG._10A

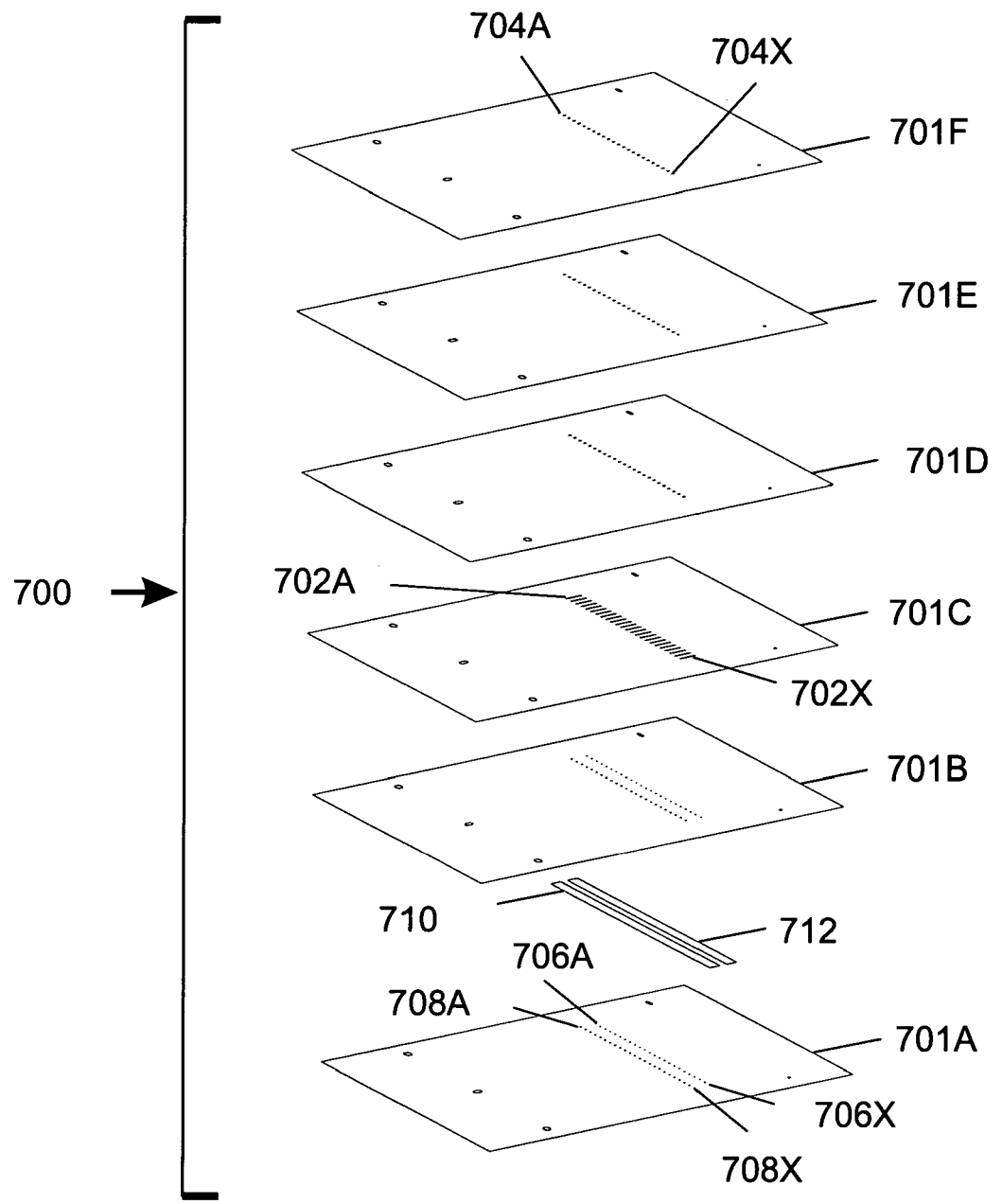
FIG._10B

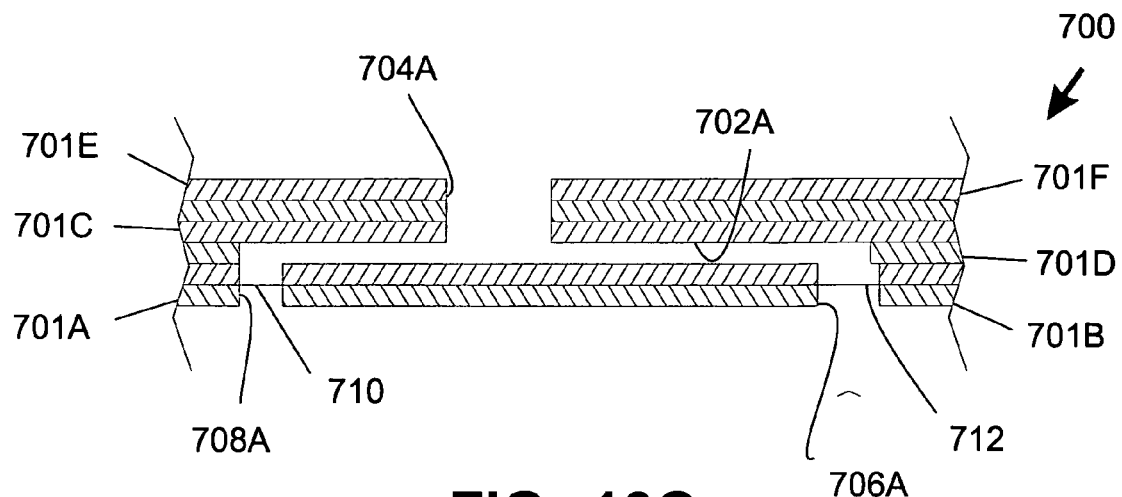
FIG._10C
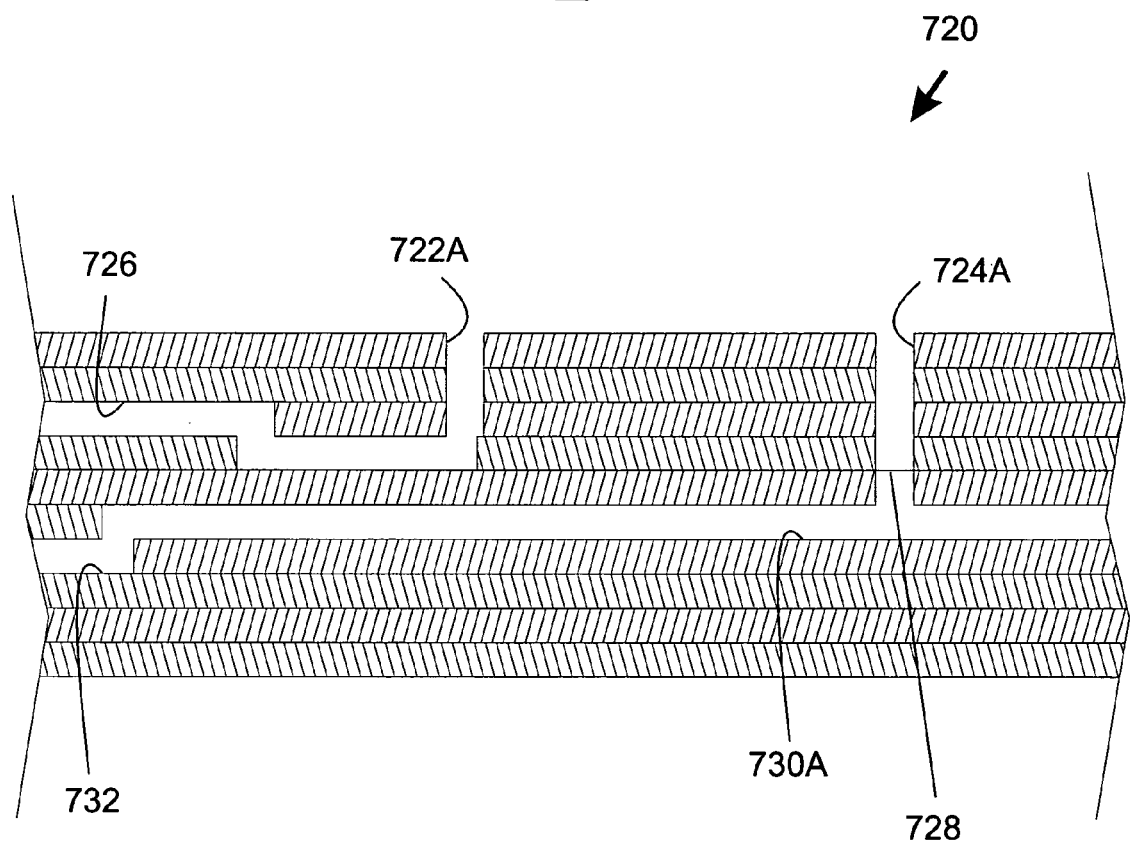
FIG._11

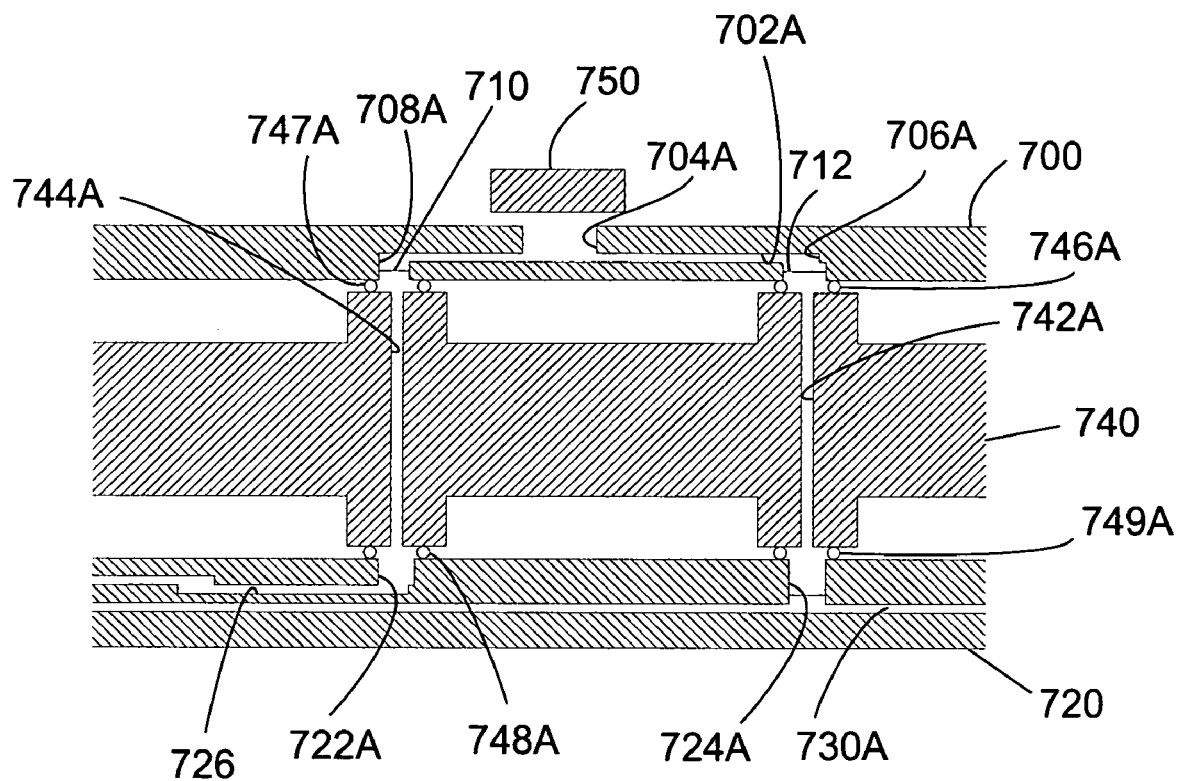
FIG._12

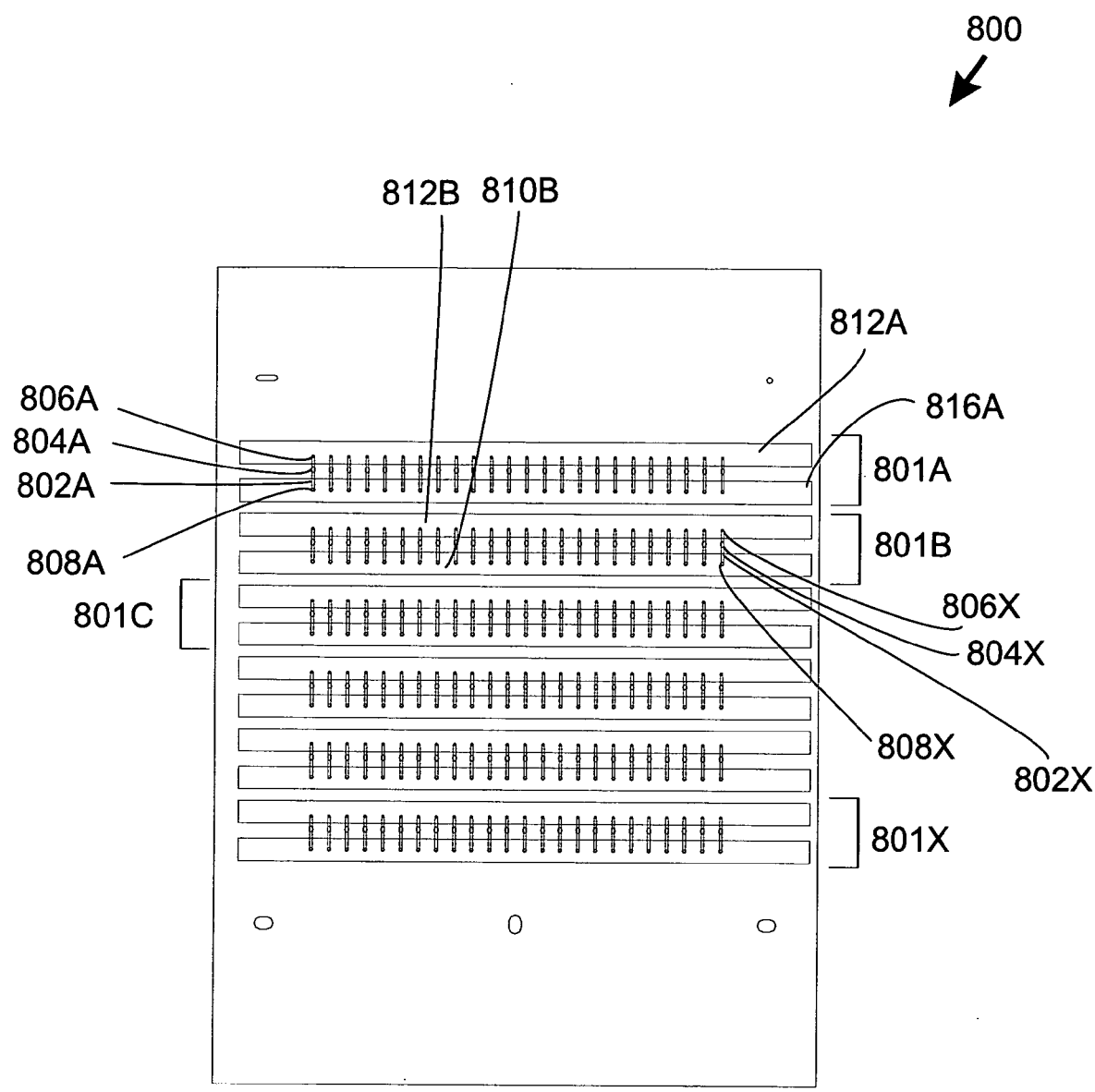
FIG._13

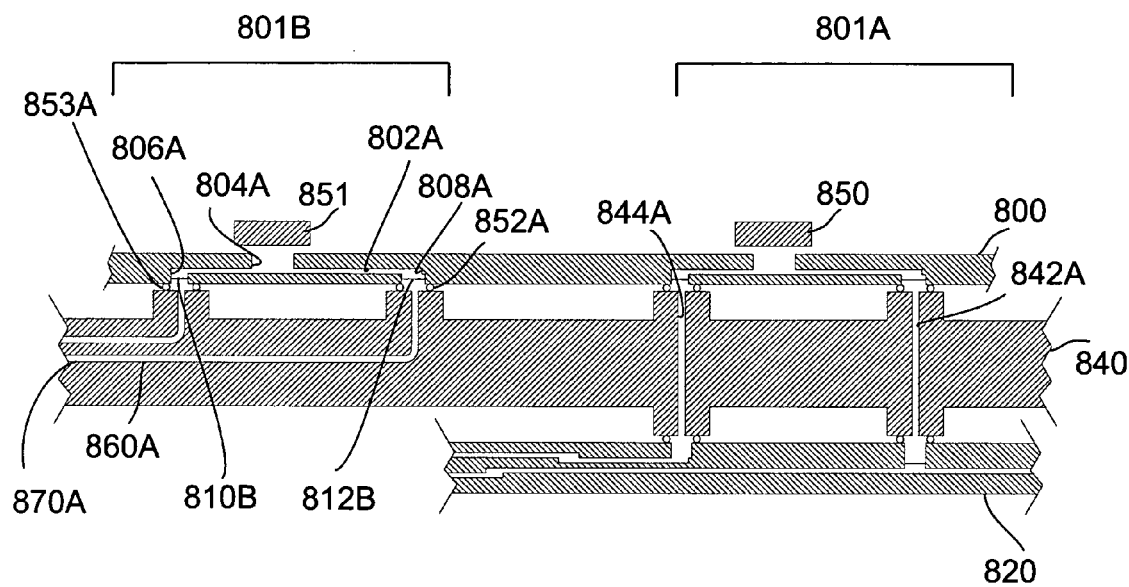
FIG._14

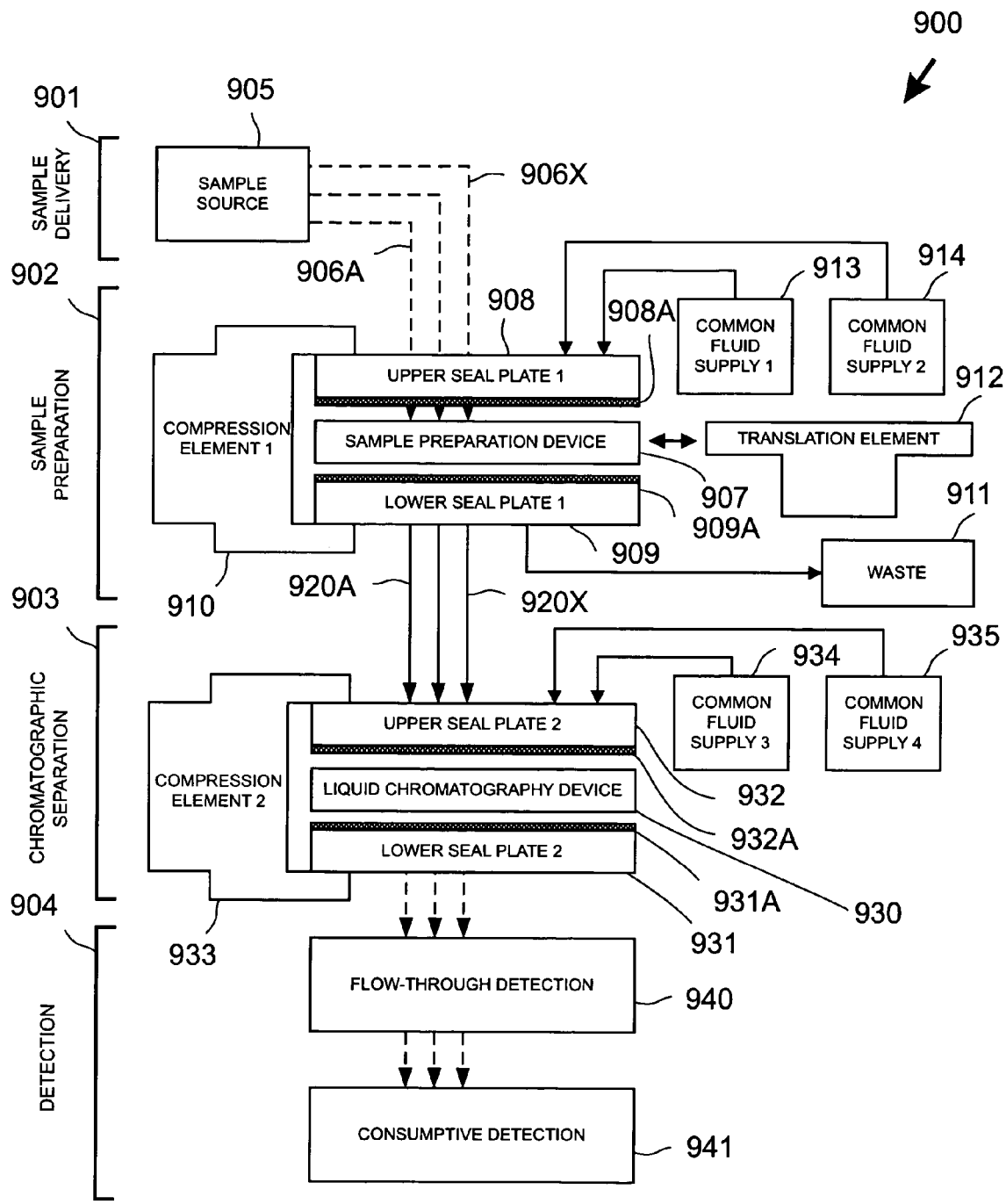
FIG._15

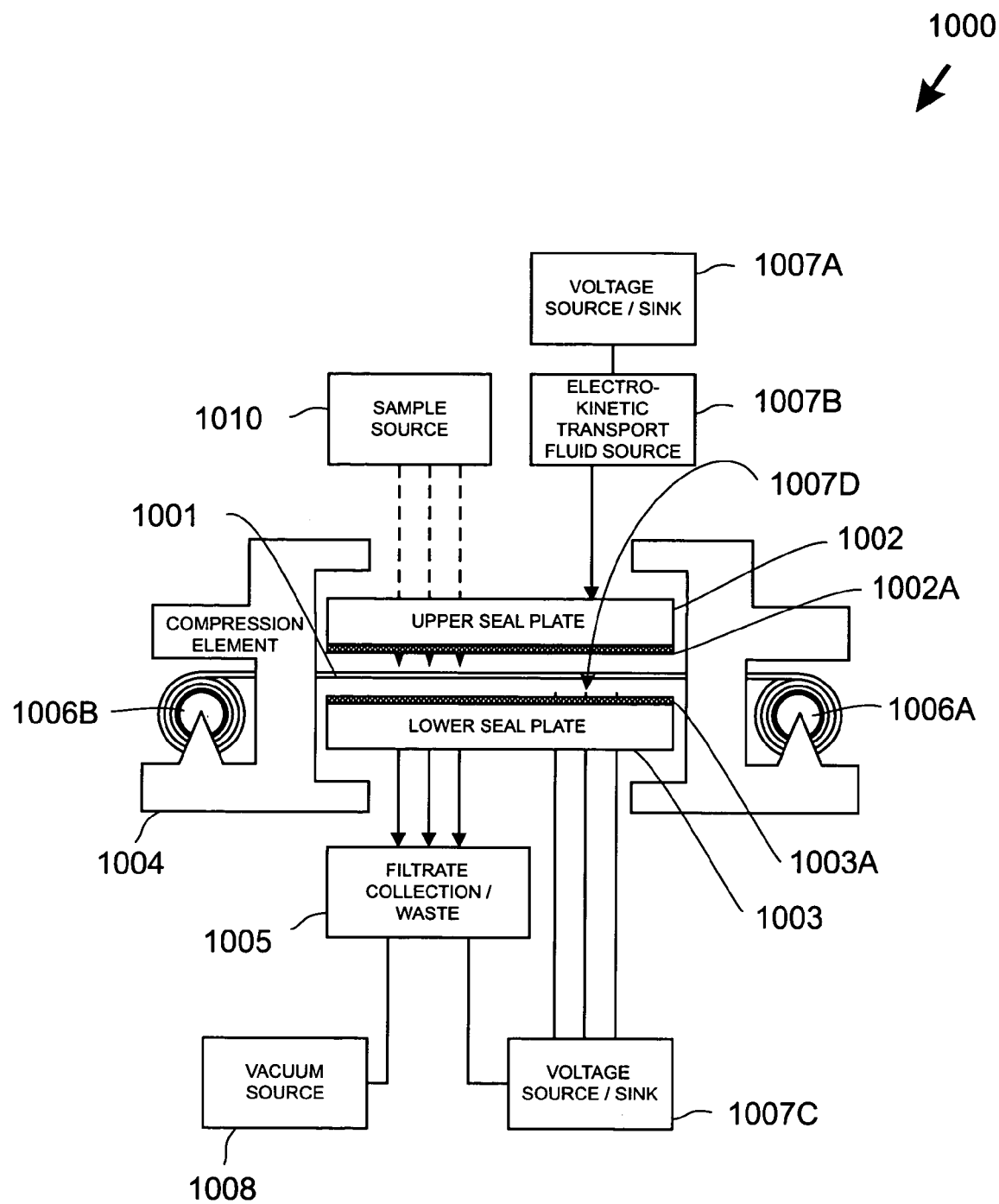
FIG._16

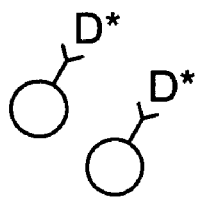
FIG._17

SAMPLE PREPARATION FOR PARALLEL CHROMATOGRAPHY

STATEMENT OF RELATED APPLICATIONS

This application claims benefit of commonly assigned U.S. Provisional Patent Application Ser. No. 60/469,476, filed May 8, 2003.

FIELD OF THE INVENTION

The present invention relates to the design, fabrication and operation of systems and devices for parallel fluid processing performed in microfluidic scale.

BACKGROUND OF THE INVENTION

Recent developments in the pharmaceutical industry and in combinatorial chemistry have exponentially increased the number of potentially useful compounds, each of which must be characterized in order to identify their active components and/or establish processes for their synthesis. To more quickly analyze these compounds, researchers have sought to automate analytical processes and to implement analytical processes in parallel. Commonly employed analytical processes include chemical or biochemical separations such as chromatographic, electrophoretic, electrochromatographic, immunoaffinity, gel filtration, and density gradient separations.

One particularly useful analytical process is chromatography, which encompasses a number of methods that are used for separating ions or molecules that are dissolved in or otherwise mixed into a solvent. Liquid chromatography ("LC") is a physical method of separation wherein a liquid "mobile phase" (typically consisting of one or more solvents) carries a sample containing multiple constituents or species through a separation medium or "stationary phase." Stationary phase material typically includes a liquid-permeable medium such as packed granules (particulate material) or a microporous matrix (e.g., porous monolith) disposed within a tube or similar boundary. The resulting structure including the packed material or matrix contained within the tube is commonly referred to as a "separation column." In the interest of obtaining greater separation efficiency, so-called "high performance liquid chromatography" ("HPLC") methods utilizing high operating pressures are commonly used.

In the operation of a separation column, sample constituents borne by mobile phase migrate according to interactions with the stationary phase, and the flow of these sample constituents are retarded to varying degrees. Individual constituents may reside for some time in the stationary phase (where their velocity is essentially zero) until conditions (e.g., a change in solvent concentration) permit a constituent to emerge from the column with the mobile phase. The time a particular constituent spends in the stationary phase relative to the fraction of time it spends in the mobile phase will determine its velocity through the column.

Early parallel LC systems that coupled multiple conventional tubular columns to common fluid supply and/or control systems provided only marginal benefits in terms of scalability and reduced cost per separation. Recent advances in microfluidic technology have allowed fabrication of microfluidic multi-column HPLC devices that permit simultaneous (parallel) separation of multiple samples while consuming very small quantities of valuable samples and solvents and generating much smaller volumes of liquid waste. Examples of such devices are disclosed in commonly assigned U.S. patent application Ser. No. 10/366,985 filed Feb. 13, 2003 (now publicly available as U.S. Patent Application Publication no. 2003/0150806), which is hereby incorporated by reference. These microfluidic devices require far fewer parts per column than conventional HPLC columns, and may be rapidly connected to an associated HPLC system without the use of threaded fittings, such as by using flat compression-type interfaces either with or without associated gaskets. A further benefit of microfluidic parallel HPLC devices is that their relatively low cost and ease of connection permits them to be disposed of after a single or only a small number of uses, thus eliminating or dramatically reducing the potential for sample carryover from one separation run to the next.

Many desirable analyses utilizing HPLC require some preparation of the sample prior to the analysis. Examples of common sample preparation processes include, without limitation, metering, pH adjustment, dilution, addition of standards, solvent extraction, addition of reagents, reconstitution, size exclusion filtration, chemical affinity filtration (including solid phase extraction), centrifugal separation, molecular weight cut-off membrane filtration, dialysis, liquid-phase extraction, protein precipitation, etc. Sample preparation may also include fluid processes such as qualitative or quantitative tests including various types of assays.

These sample preparation steps often may be time consuming, labor intensive, and create the opportunity for error to be introduced (e.g., by incorrect measurement of quantities or concentrations). It is relatively simple to prepare samples for analysis in single-column HPLC systems using conventional laboratory techniques and equipment. Extending such preparations to multi-column (e.g., parallel) HPLC systems, however, is significantly more challenging due to the sheer volume of samples that must be prepared simultaneously to take advantage of high throughput capacity of microfluidic parallel HPLC devices. For example, if multi-column HPLC system can process twenty-four samples in a single run, twenty-four samples must be prepared prior to initiating the run. If samples are processed serially, the cycle time associated with the sample preparation process could eliminate the time savings provided by the parallel analysis. In addition, a first set of prepared samples could degrade, evaporate, or otherwise be damaged while awaiting preparation of the remaining samples for a particular run.

Moreover, traditional sample preparation processes and devices are designed for conventional scale (i.e., non-microfluidic) laboratory devices. Thus, while microfluidic parallel HPLC devices or other synthesis and/or analytical systems may require only very small sample volumes, conventional sample preparation processes and devices typically create large volumes of sample, much of which would be discarded as waste if such prepared samples were supplied to microfluidic systems. Because samples may often include scarce and costly chemicals, such waste would be undesirable. Additionally, samples often contain hazardous or toxic materials with their attendant safety and disposal concerns. In addition, traditional sample preparation devices may be complex and expensive to manufacture. As a consequence, economical operation may require devices to be cleaned and re-used, further increasing the procedures required to cycle the instruments and related equipment.

Thus, it would be desirable to provide microfluidic devices for preparing samples for analysis in microfluidic parallel HPLC devices. It would also be desirable to provide microfluidic devices for preparing substantially all samples to be used in a particular analysis operation simultaneously to minimize sample degradation or other detrimental effects of prolonged delays prior to the (e.g., serial) analysis of individual samples. If would further be desirable to provide microfluidic devices capable of performing sample preparation processes while minimizing the consumption of samples and reagents. It would also be desirable to provide microfluidic devices for preparing multiple sample sets simultaneously to minimize cycle times between analysis runs. It would further be desirable to provide a system capable of preparing a set of samples while another set of (previously prepared) samples is being analyzed to minimize delays between analytical runs. It would also be desirable to provide microfluidic sample preparation devices that are easily fabricated and disposable.

BRIEF DESCRIPTION OF THE DRAWINGS

FIG. 1B is a top view block diagram of a portion of the microfluidic device of FIG. 1A.

FIG. 1C is a partial cross-sectional view of a portion of the microfluidic device of FIG. 1B.

FIG. 2 is a top view block diagram of a portion of an alternate embodiment of the microfluidic device according to the present invention.

FIG. 3 is a top view block diagram of a portion of an alternate embodiment according to the present invention.

FIG. 4A is a block diagram of a portion of an alternate embodiment of a microfluidic device according to the present invention, shown in a first operational state.

FIG. 4B is a block diagram of a portion of the microfluidic device of FIG. 4A, shown in a second operational state.

FIG. 4C is a block diagram of a portion of the microfluidic device of FIG. 4A, shown in a third operational state.

FIG. 5A is a block diagram of a portion of an alternate embodiment of the microfluidic device according to the present invention, shown in a first operational state.

FIG. 5B is a block diagram of a portion of the microfluidic device of FIG. 5A, shown in a second operational state.

FIG. 5C is a block diagram of a portion of the microfluidic device of FIG. 5A, shown in a third operational state.

FIG. 6 is a top view of a microfluidic device according to another embodiment of the invention.

FIG. 7A is a block diagram of a portion of the microfluidic device of FIG. 6.

FIG. 7B is a block diagram of the microfluidic device of FIG. 7A, shown in a second operational state.

FIG. 7C is a block diagram of the microfluidic device of FIG. 7A, shown in a third operational state.

FIG. 7D is a block diagram of the microfluidic device of FIG. 7A, shown in a fourth operational state.

FIG. 8A is a block diagram of a portion of an alternate embodiment of the microfluidic device according to the invention.

FIG. 8B is a side cross-section view of a portion of the device of FIG. 8A.

FIG. 9A is a block diagram of a portion of an alternate embodiment of the microfluidic device according to the invention, shown in a first operational state.

FIG. 9C is a block diagram of the microfluidic device of FIG. 9A, shown in a third operational state.

FIG. 10A is a top view of microfluidic sample preparation device according to the present invention.

FIG. 10B is an exploded perspective view of the microfluidic sample preparation device of FIG. 10A.

FIG. 10C is a partial cross-sectional view of the microfluidic sample preparation device of FIG. 10A taken across line "A"—"A."

FIG. 11 is a partial cross-sectional view of the sample injection region of a multi-layer, multi-column HPLC device.

FIG. 12 is a partial cross-sectional view of and interface for mating the sample preparation device of FIGS. 10A–10C and the multi-layer, multi-column HPLC device of FIG. 11.

FIG. 13 is a top view of another embodiment of a microfluidic sample preparation device according to the present invention.

FIG. 14 is a partial cross-sectional view of and interface for mating the sample preparation device of FIG. 13 and the multi-layer, multi-column HPLC device of FIG. 11.

FIG. 15 is a schematic showing interconnections of various components of a first high throughput analytical system according to the present invention.

FIG. 16 is a schematic showing interconnections of various components of the sample preparation portion of second high throughput analytical system according to the present invention.

FIG. 17 is a schematic illustration of reagents and products of a parallel sandwich-type (affinity) assay.

DETAILED DESCRIPTION OF PREFERRED EMBODIMENTS OF THE INVENTION

Definitions

Figure 1A:
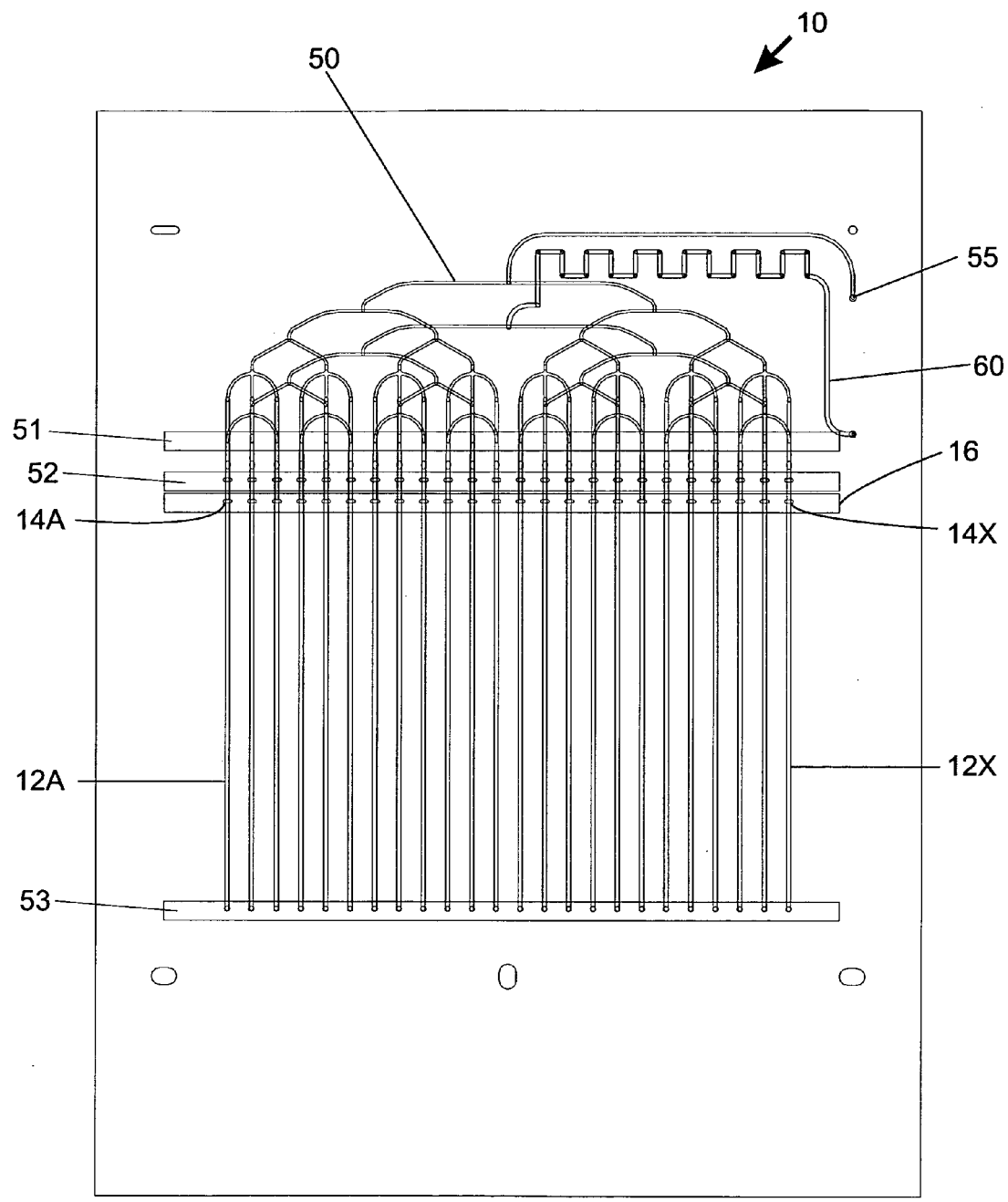
FIG. 1A is a top view of a microfluidic device according to the present invention.

The term "analysis" refers to the separation, extraction, purification, and/or identification of one or more ingredients of a substance.

The terms "channel" or "chamber" as used herein are to be interpreted in a broad sense. Thus, they are not intended to be restricted to elongated configurations where the transverse or longitudinal dimension greatly exceeds the diameter or cross-sectional dimension. Rather, such terms are meant to comprise cavities or tunnels of any desired shape or configuration through which liquids may be directed. Such a fluid cavity may, for example, comprise a flow-through cell where fluid is to be continually passed or, alternatively, a chamber for holding a specified, discrete ratio of fluid for a specified ratio of time. "Channels" and "chambers" may be filled or may contain internal structures comprising, for example, valves, filters, and similar or equivalent components and materials.

The terms "chromatography column" and "column" are used interchangeably herein and refer to a device or portion thereof comprising stationary phase material that is capable of separating at least a portion of an analyte in a fluid.

The terms "stencil" or "stencil layer" as used herein refers to a preferably substantially planar material layer or sheet through which one or more variously shaped and oriented portions have been cut or removed through the entire thickness of the layer, and which removed portions permit substantial fluid movement within the layer (as opposed to simple through-holes or vias for transmitting fluid from one layer to another layer). The outlines of cut or removed portions form the lateral boundaries of microstructures that are formed when a stencil is sandwiched between other layers such as substrates or other stencils.

The term "parallel" as used herein refers to the ability to concomitantly or substantially concurrently process two or more separate fluid volumes, and does not necessarily refer to a specific channel or chamber structure or layout.

Microfluidic Devices Generally

In an especially preferred embodiment, microfluidic devices according to the present invention are constructed using stencil layers or sheets to define channels and/or chambers. As noted previously, a stencil layer is preferably substantially planar and has a channel or chamber cut through the entire thickness of the layer to permit substantial fluid movement within that layer. Various means may be used to define such channels or chambers in stencil layers. For example, a computer-controlled plotter modified to accept a cutting blade may be used to cut various patterns through a material layer. Such a blade may be used either to cut sections to be detached and removed from the stencil layer, or to fashion slits that separate regions in the stencil layer without removing any material. Alternatively, a computer-controlled laser cutter may be used to cut portions through a material layer. While laser cutting may be used to yield precisely dimensioned microstructures, the use of a laser to cut a stencil layer inherently involves the removal of some material. Further examples of methods that may be employed to form stencil layers include conventional stamping or die-cutting technologies, including rotary cutters and other high throughput auto-aligning equipment (sometimes referred to as converters). The above-mentioned methods for cutting through a stencil layer or sheet permits robust devices to be fabricated quickly and inexpensively compared to conventional surface micromachining or material deposition techniques that are conventionally employed to produce microfluidic devices.

After a portion of a stencil layer is cut or removed, the outlines of the cut or otherwise removed portions form the lateral boundaries of microstructures that are completed upon sandwiching a stencil between substrates and/or other stencils. The thickness or height of the microstructures such as channels or chambers can be varied by altering the thickness of the stencil layer, or by using multiple substantially identical stencil layers stacked on top of one another. When assembled in a microfluidic device, the top and bottom surfaces of stencil layers are intended to mate with one or more adjacent layers (such as stencil layers or substrate layers) to form a substantially enclosed device, typically having at least one inlet port and at least one outlet port.

A wide variety of materials may be used to fabricate microfluidic devices having sandwiched stencil layers, including polymeric, metallic, and/or composite materials, to name a few. Various preferred embodiments utilize porous materials including filtration media. Substrates and stencils may be substantially rigid or flexible. Selection of particular materials for a desired application depends on numerous factors including: the types, concentrations, and residence times of substances (e.g., solvents, reactants, and products) present in regions of a device; temperature; pressure; pH; presence or absence of gases; and optical properties. For instance, particularly desirable polymers include polyolefins, more specifically polypropylenes, and vinyl-based polymers.

Various means may be used to seal or bond layers of a device together. For example, adhesives may be used. In one embodiment, one or more layers of a device may be fabricated from single- or double-sided adhesive tape, although other methods of adhering stencil layers may be used. Portions of the tape (of the desired shape and dimensions) can be cut and removed to form channels, chambers, and/or apertures. A tape stencil can then be placed on a supporting substrate with an appropriate cover layer, between layers of tape, or between layers of other materials. In one embodiment, stencil layers can be stacked on each other. In this embodiment, the thickness or height of the channels within a particular stencil layer can be varied by varying the thickness of the stencil layer (e.g., the tape carrier and the adhesive material thereon) or by using multiple substantially identical stencil layers stacked on top of one another. Various types of tape may be used with such an embodiment. Suitable tape carrier materials include but are not limited to polyesters, polycarbonates, polytetrafluoroethlyenes, polypropylenes, and polyimides. Such tapes may have various methods of curing, including curing by pressure, temperature, or chemical or optical interaction. The thickness of these carrier materials and adhesives may be varied.

Device layers may be directly bonded without using adhesives to provide high bond strength (which is especially desirable for high-pressure applications) and eliminate potential compatibility problems between such adhesives and solvents and/or samples for example, in one embodiment, multiple layers of 7.5-mil (188 micron) thickness "Clear Tear Seal" polypropylene (American Profol, Cedar Rapids, Iowa) including at least one stencil layer may be stacked together, placed between glass platens and compressed to apply a pressure of 0.26 psi (1.79 kPa) to the layered stack, and then heated in an industrial oven for a period of approximately five hours at a temperature of 154° C. to yield a permanently bonded microstructure well-suited for use with high-pressure column packing methods. In another embodiment, multiple layers of 7.5-mil (188 micron) thickness "Clear Tear Seal" polypropylene (American Profol, Cedar Rapids, Iowa) including at least one stencil layer may be stacked together. Several microfluidic device assemblies may be stacked together, with a thin foil disposed between each device. The stack may then be placed between insulating platens, heated at 152° C. for about 5 hours, cooled with a forced flow of ambient air for at least about 30 minutes, heated again at 146° C. for about 15 hours, and then cooled in a manner identical to the first cooling step. During each heating step, a pressure of about 0.37 psi (2.55 kPa) is applied to the microfluidic devices.

Notably, stencil-based fabrication methods enable very rapid fabrication of devices, both for prototyping and for high-volume production. Rapid prototyping is invaluable for trying and optimizing new device designs, since designs may be quickly implemented, tested, and (if necessary) modified and further tested to achieve a desired result. The ability to prototype devices quickly with stencil fabrication methods also permits many different variants of a particular design to be tested and evaluated concurrently.

Further embodiments may be fabricated from various materials using well-known techniques such as embossing, stamping, molding, and soft lithography.

In addition to the use of adhesives and the adhesiveless bonding method discussed above, other techniques may be used to attach one or more of the various layers of microfluidic devices useful with the present invention, as would be recognized by one of ordinary skill in attaching materials. For example, attachment techniques including thermal, chemical, or light-activated bonding steps; mechanical attachment (such as using clamps or screws to apply pressure to the layers); and/or other equivalent coupling methods may be used.

Preferred Embodiments

Systems and devices as described herein may be used for preparing samples for chromatographic separations and then chromatographically separating the prepared samples, preferably in a high-throughput fashion utilizing multiple parallel first (fluid) processing regions in fluid communication with multiple parallel second (fluid) processing regions wherein the each second processing region includes a chromatography column. Additionally, one or more common fluid supplies may be utilized in each of the sample preparation and separation steps to minimize the number of requisite fluid connections and external components such as pumps, reservoirs, pulse dampers, flow controllers, and the like.

Sample preparation may include any of various fluid processing steps suitably performed prior to liquid chromatographic separation. Common sample preparation steps includes various forms of filtration (e.g., size exclusion, ion exchange, etc.), separation using media containing specific- and non-specific binding receptors, incubation, and similar commonly performed preparatory processes. Additionally, sample preparation as described herein is intended to include the performance of various qualitative or quantitative tests such as assays suitably performed in advance of liquid chromatographic separation.

Types of porous elements that may be used for sample preparation include, but are not limited to, regions packed with particulate material (e.g., conventional chromatographic separation material), porous monoliths, and porous membranes. Examples of various types of porous membranes that may be used in sample preparation devices include: regenerated cellulose, nylon, polytetrafluoroethylene (PTFE), polyvinylidene fluoride (PVDF), polypropylene, glass microfiber, cellulose acetate, and polyethersulfone. Molecules or other moeties for performing specific- or non-specific binding may be added to porous elements where desired to isolate particular types of materials from a given sample.

In certain embodiments, a sample preparation device generally functions to separate a sample into retentate, which is retained by the separation media, and filtrate, which passes through the filtration media. Analytes of interest may be contained in either the retentate or filtrate, depending on the particular application. Thus, if the filtrate contains the analytes of interest, then the filtrate may be subjected to chromatographic analysis while the retentate is discarded; or, if the retentate contains the analytes of interest, then the filtrate may be discarded while the analytes retained by the retentate may be re-suspended or flushed from the filtrate with the aid of an added solvent or other appropriate means.

Various types of transport means may be utilized with a sample preparation device to motivate the passage of samples through sample preparation elements. In one embodiment, one or more pressurized fluid(s) may be supplied to samples by one or more pump(s) or other pressurized fluid source(s) to carry or "push" samples through preparative media. One potential advantage of using pressurized fluids is that high pressure differentials (e.g., equivalent to many atmospheres) may be generated. In another embodiment, one or more vacuum source(s) may be used to draw samples through preparative media. While the pressure differential of a vacuum system is limited to within one atmosphere, a potential advantage of using vacuum is that dilution of the samples may be minimized. In another embodiment, samples may be transported through preparative media electrokinetically with the application of a voltage differential.

In one embodiment, a microfluidic sample preparation device fabricated with a plurality of device layers, including at least one stencil layer, defines multiple microfluidic sample preparation elements. Each sample preparation element preferably includes a porous element of a similar type. The sample preparation elements may be adapted to perform one or more steps, which may occur continuously, selectively, periodically, or require incubation. In a particularly preferred embodiment, a sample preparation device includes multiple sets of parallel sample preparation elements, with each set of sample preparation elements adapted to process multiple samples in parallel. The design and fabrication of multi-layer microfluidic devices is described in commonly assigned U.S. patent application Ser. No. 10/366,985, filed Feb. 13, 2003 (now publicly available as U.S. Patent Application Publication no. 2003/0150806) and U.S. patent application Ser. No. 10/696,354, filed Oct. 28, 2003, which is hereby incorporated by reference. Microfluidic sample preparation devices according to the present invention may be integrated with multiple HPLC separation columns, also defined in the plurality of device layers, as illustrated in FIGS. 1A–9C. Alternatively, microfluidic sample preparation devices according to the present invention may be adapted to interface with multiple HPLC separation columns, as illustrated in FIGS. 10A–16.

In one embodiment, a microfluidic device for performing liquid chromatography includes porous membranes, frits, secondary packed columns, or other structures (collectively referred to as "filters") adapted to purify multiple samples prior to their injection into multiple parallel HPLC columns. The filters may provide one or more functions, including filtering of large particles that might clog the column, desalting of the column, specific binding of certain materials based on chemical or biological affinity, and other desirable functions. Each HPLC column preferably has at least one associated filter. In one embodiment, each HPLC column preferably has at least two associated filters.

FIG. 1A shows a multi-layer, stencil-based liquid chromatography device 10 having multiple liquid chromatography columns 12A–12X. (Although FIG. 1A shows the device 10 having twenty-four columns 12A–12X, it will be readily apparent to one of ordinary skill in the art that any number of columns 12A–12X may be provided. For this reason, the designation "X" is used to represent the last column 12X, with the understanding that "X" represents a variable and could represent any desired number of columns. This convention is used throughout this document.) As described in the above-referenced patent applications, the columns 12A–12X are packed with a stationary phase material through a packing 50. The stationary phase is retained within the device 10 by a plurality of frits 51–53. The packing manifold 50 may be sealed by closing the packing inlet 55 by any suitable means, such as cauterization, application of an adhesive tape, or injection of an epoxy or other suitable sealant. Alternatively, a secondary stream of mobile phase may be injected into the device 10 through the packing manifold 50 during operation of the device 10 to maintain the packing integrity of the stationary phase material within the device 10. A mobile phase manifold 60 also is provided. Each column 12A–12X includes a sample injection port 14A–14X. A porous membrane 16 is disposed between the injection ports 14A–14X and the columns 12A–12X.

FIG. 1B is a representation of the sample injection portion a single column 12A shown in block diagram form for simplicity. In operation, a sample 17A is injected into the sample injection port 14A. The membrane 16 acts to prevent contaminant particles 18A above a certain size (i.e., larger than the average pore size of the filter 16) from entering the columns 12A–12X. Thus, large particles 18A (such as debris, proteins, cells, or undesirable contaminants) are prevented from contaminating the column 12A or adversely affecting the chromatographic separation. Particles 20, which are smaller than the average pore size of the filter membrane 16, pass into the column 12A to be separated. In this manner, the membrane 16 acts as a size exclusion filter. As shown in FIG. 1C, the porous membrane 16 is positioned between the stencil layers 50, 51, which, together with the device layers 60, 61, define the column 12A and the injection channel 13A. The incorporation of membranes in multi-layer microfluidic structures is described in commonly assigned U.S. patent application Ser. No. 10/256,505, filed Sep. 27, 2002 (now publicly available as U.S. Patent Application Publication No. 2003/0150792), the entirety of which is incorporated herein by reference.

Although FIG. 1A illustrates the columns 12A–12X and injection ports 14A–14X as being stacked, or super-imposed, it will be readily understood by one of ordinary skill in the art that many geometric arrangements of columns, separation ports, and membranes may be selected as desired and appropriate for different applications. Additionally, the porosity of the membrane 16 may be selected to provide any desired filter resolution. Further, the membrane 16 may provide certain desirable characteristics for filtering by means other than size exclusion, such as chemical affinity, specific binding, ion exchange, and other useful interactions.

For example, in an alternate embodiment illustrated in FIG. 2, multiple sample inlet ports 14A, 15A may be associated with a single column 12A. Thus, the column 12A may be used to perform separations of multiple samples 17A, 17B. A first filtration and separation is performed using the first inlet port 14A, as described above. Once the first filtration and separation is complete, a second sample 17B is injected into the second sample port 15A. Contaminants 18B are filtered by the porous membrane 16A and the filtered sample 21 is injected onto the column 12A to undergo separation. Because multiple sample inlet ports 14A, 15A are provided, contaminants 18A filtered from a first sample 17A will not interact with a second sample 17B, thus minimizing the risk of erroneous results arising from chemical interactions, carryover, or contamination between various samples.

In another example, illustrated in FIG. 3, a contaminant wash injection channel 22A is provided to allow the membrane 16 to be washed and re-used. In this embodiment, a sample 17A is injected through the port 14A, through the membrane 16 and onto the column 12A. Contaminants 18 are retained by the membrane 16 while the filtered sample 20 travels to the separation column 12A. The contaminant wash injection channel 22A is located on the column 12A side of the membrane 16 and may be isolated with a valve or other closure mechanism (not shown). An exit channel 24, also valved or otherwise controlled, is provided on the sample injection port 14A side of the membrane 16. Once the separation is complete, a solvent stream 26 is pushed from the inlet channel 22A, through the membrane 16, and out the exit channel 24. The contaminants 18 that were filtered by the membrane 16 are washed off and out the exit channel 24, thus enabling the membrane 16, and hence, the injection port 14A and the column 12A, to be re-used.

In another embodiment, shown in FIGS. 4A–4D, a structure, similar to that shown in FIGS. 1A–1C, is provided having a chromatography column 112A, a porous membrane 116, and a sample injection port 114A. In addition, a secondary mobile phase channel 115 is provided. The porous membrane 116 is adapted to perform a chemical or biochemical extraction. For instance, the membrane 116 may be an ion binding membrane where molecules with a certain charge bind to the material. Alternatively, the membrane 116 may be an affinity membrane adapted to attract specific molecules based on any number of properties. In another embodiment, the membrane 116 may contain specific receptors attached (for example anti-bodies) adapted to bind to biological or chemical moieties. For example, the membrane 116 may be used to enhance the resolving power of the chromatography column 112A. A sample 120 containing a complex mixture of proteins (122, 124) is injected into port 114A at a pH of about seven. The membrane 116 is fabricated with a material that is positively charged at the selected pH. As a consequence, any negatively charged proteins 122 in the sample 120 are retained by the membrane 116 (and thus prevented from entering the column 112A), as shown in FIG. 4A. A reverse-phase or any other desirable separation may then be performed on only the positively charged proteins 124 contained in the sample 120, such as shown in FIG. 4B. After completion of the separation, a high pH solution may be provided through the channel 115 and passed across the membrane 116, thereby releasing the negatively charged proteins 122, which then pass into the column 112A whereupon another separation may be performed as shown in FIG. 4C.

Referring to FIGS. 5A–5C, another embodiment, similar to the embodiment discussed above with respect to FIGS. 4A–4C includes a separate waste port 130. A first separation on positively charged molecules 124 is performed as described above. However, the negatively charged molecules 122 are not injected into the column 112A, but instead are washed out through the waste port 130 once the separation of the positively charged molecules 124 is complete. In this manner, the system is flushed and prepared for new sample 120 and minimizing the risk of sample-to-sample contamination.

Such embodiments may be used to perform the bind-and-elute step typically used in DNA/RNA purification. A sample is passed through a porous membrane material that binds the molecules to be studied. The remaining solution is sent to waste. A different elution fluid which liberated the bound molecules from the porous membrane may be used to extract the sample from the membrane and carry it into the HPLC column where it is separated.

In another embodiment, shown in FIGS. 6, 7A–8E, and 8A–8B, packed columns may be placed in series to provide the desired preparation of a sample prior to separation. Referring to FIG. 6, a microfluidic device 300 includes multiple chromatography columns 302A–302N and sample injection ports 304A–304X. A column packing manifold 306 is also provided. Each of the columns 302A–302X is filled with the desired stationary phase material through the manifold 306. Notably, the manifold 306 is in fluid communication with the columns 302A–302X by way of the packing ports 308A–308X, which are disposed between either end of the columns 302A–302X. In this manner, different stationary phase materials may be serially packed in the columns 302A–302X to provide a pre-column or guard column portion, which acts to prepare a sample before it enters the remainder of the column.

The point of intersection (i.e., the packing port 308A) between the packing manifold 306 and the column 302A is positioned at an intermediate point between a first end 301A and a second end 301B of the column 302A, as shown in FIG. 7A. As shown in FIG. 7B, the column 302A may then be packed with a first stationary phase material 320. As shown in FIG. 7C, a portion of the stationary phase material may then be evacuated from the column 302A through an evacuation port 318A. Alternatively, a fluid flow may be provided through the evacuation port 318A during the packing of the first stationary phase material 320 to direct all such material into the upper portion of the column 320A. As shown in FIG. 7D, a second stationary phase material 322 may then be introduced in a similar manner, filling the remaining portion of the column 320A. As a result, the column 320A includes two separate stationary phase regions in series—a "pre-column" 321 and the column 323.

It will be apparent to one of ordinary skill in the art that the pre-column may be used to prepare the samples being separated in any desirable manner, including, but not limited to the techniques described above. Any suitable combination of stationary phase materials may be used to achieve the desired results. As illustrated in FIG. 6, the packing ports 308A–308X are located very near the termini of the columns 302A–302X; however, it will be apparent to one of ordinary skill in the art that the packing ports 308A–308X may be located at any desirable point along the columns 302A–302X so that the pre-column and column portions may have any desired or appropriate length within the overall column 302A–302X.

In another embodiment, shown in FIGS. 8A–8B (which show a single channel of a multi-channel device 400, for clarity), a pre-column 403A and column 402A are provided. The pre-column 403A may be packed with a first stationary phase material 422 through a packing channel 407 at a packing port 409. The column 402A may be packed with a second stationary phase material 420 through a packing channel 406 at a packing port 408. The pre-column 403A is in fluid communication with the column 402A at an intersection 416 and across a porous membrane or "frit" 418. The frit 418 prevents the stationary phase material in the column 402A from traveling into the pre-column 403A and vice-versa. It will be apparent to one of ordinary skill in the art that the pre-column 403A may be used to prepare the samples being separated in any desirable manner, including, but not limited to the techniques described above. Any suitable combination of stationary phase materials may be used to achieve the desired results.

In another embodiment, a sample is prepared by adding a quantified amount of a solution or solvent to the sample prior to injection into an operative region of a device. One or more samples may be prepared simultaneously or in series. The solution or solvent may be added to dilute the concentration of a sample prior to injection. Alternatively, the solution may be added to the sample to perform a chemical or biochemical reaction. In another embodiment, the solution may be used to alter the pH of the sample.

Figure 9B:
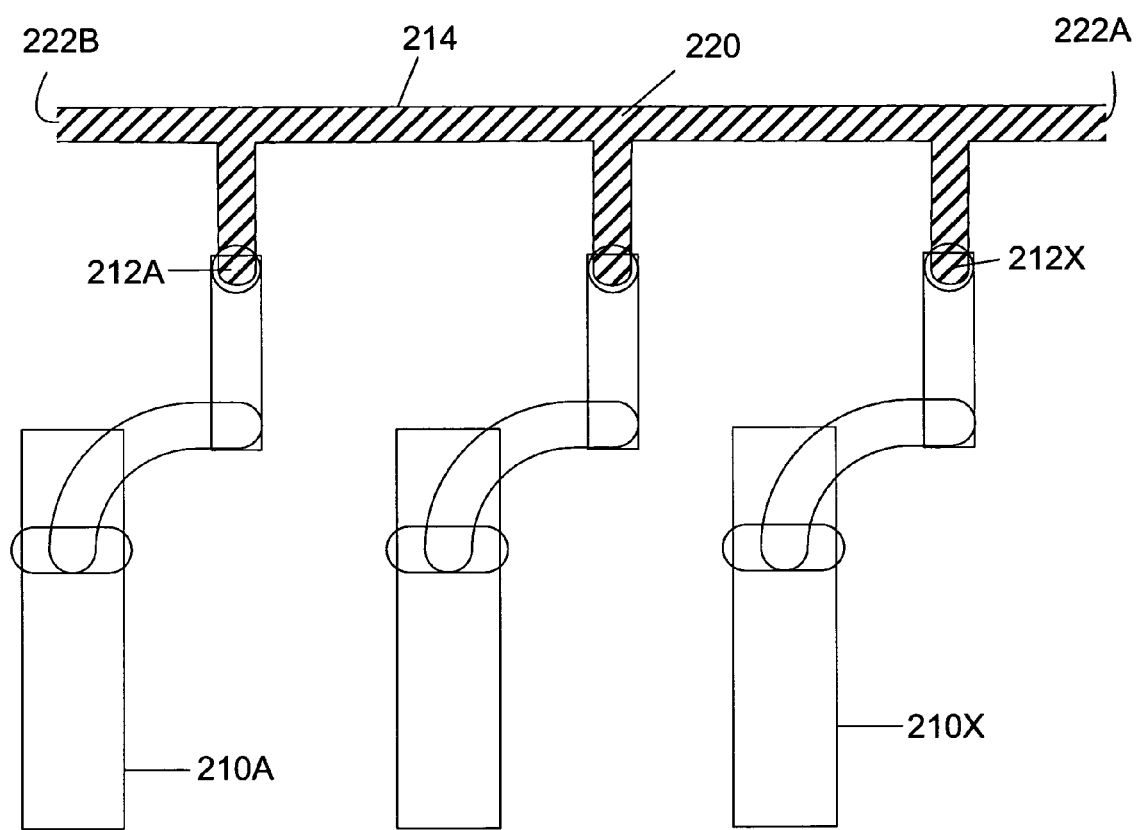
FIG. 9B is a block diagram of the microfluidic device of FIG. 9A, shown in a second operational state.

As shown in FIGS. 9A–9C, a microfluidic device 200 includes multiple separation columns 210A–210X adapted for performing parallel separations, each column 210A–210X having an independent sample injection port 212A–212X. Also provided is a trunk channel 214 having a plurality of branch channels 216A–216X in fluid communication with the injection ports 212A–212X and the columns 210A–210X. A solution 220 to be combined is injected at a first port 222A, filling the trunk channel 214 and branch channels 216A–216X. Sufficient solution 220 is provided to fill the branch channels 216A–216X completely. Excess solution 220 may be prevented from exiting the device 200 through the injection ports 212A–212X through any desirable means including, but not limited to, capillary breaks, valves (on-board or off-board), porous membrane, compressed gaskets, or other suitable mechanism. An evacuation port 222B is then opened and the solution 220 contained in the trunk channel 214 is evacuated while a portion thereof remains in the branch channels 216A–216X to form fluid plugs 220A–220X. Because the volume of each branch channel 216A–216X is known, each plug 220A–220X has a predetermined volume. Samples 230A–230X may then be introduced into the sample injection ports 212A–212X. The injection ports 212A–212X and evacuation port 222A may then be sealed and the pressure within the trunk channel 214 increased so that the solution 220 mixes with the samples 230A–230X. Once the solution 220 mixes with the samples 230A–230X, the trunk channel 214 may be pressurized (with any suitable fluid, such as a gas or a mobile phase material) to force the mixture into the HPLC columns 210A–210X for separation.

Microfluidic devices and systems according to the present invention also may be used to perform other useful sample preparations. For example, sample preparation may include a stability reaction in which compounds of interest are incubated in a variety of incubation solutions. HPLC separation and detection is then performed on each incubated solution to determine if the incubation solution changed the molecules of interest.

Incubation may be performed using any of the previously described embodiments. For example, the sample injection ports of the embodiments shown in FIGS. 1A–1C, 2, 3, and 4A–4C may be proportioned to accommodate a sample and an incubation solution. The two fluids are mixed and incubated for a desired period of time. Thereafter, a HPLC separation is performed on the incubated solution. In such embodiments, any combination of samples and incubation solutions may be provided in any number of separation columns. If a device such as that shown in FIGS. 9A–9C is used, multiple samples may be injected into separate sample injection inlets while a single incubation solution is delivered through the trunk/branch channel network. In this manner, multiple samples may be subjected to the same incubation solution simultaneously. Alternatively, multiple incubation solutions may be injected into the sample injection ports and a single sample compound delivered through the trunk/branch channel network, thereby subjecting a single sample to any number of desirable incubation experiments.

Certain embodiments may be used to perform analyte tagging. It is often desirable to chemically tag a sample prior to introducing it into a HPLC column. As will be readily apparent to one of ordinary skill in the art, such tags may provide a variety of functions, such as a detection label for fluorescence or mass spectrometry analysis. Alternatively, the tag can serve to more effectively resolve the molecules during separation. For example, a solvent added to the sample may contain a chemically or biologically active tag that will either permanently or semi-permanently interact with some or all of the molecules in the sample. The solvent and sample are mixed and allowed to interact for a period of time. The sample may be heated or otherwise subjected to stimulus to enhance the desired interaction. The sample may then be passed through a filter to remove any unbound tagging material. Alternatively, the entire sample is simply injected onto the HPLC column where the unbound tag elutes at a different time.

Certain embodiments also may be used to perform enzymatic assays. Currently, enzymatic assays are often performed in a "homogenous" format when done in high throughput. In this format, assay development is conducted to learn how to "tag" the enzyme so that the tag is optically active and will change its properties a molecule is added to the solution that interacts with the enzyme. Then, the assays can be performed in well-plates at very high throughput using robots to dispense the tagged enzymes and molecules of interest. These plates are then read using optical readers. A significant limitation of this approach is that the assay development step is very slow and labor intensive. A way to perform the assays at high throughput without needed to tag the enzymes would be much more preferable.

Thus, in certain embodiments, enzymes and target molecules may be combined as described above, and allowed to incubate. The amount of the target molecule may be serially diluted prior to incubation with the enzyme to perform an IC 50 curve. Serial dilution may be performed using conventional techniques. Alternatively, a microfluidic serial dilution device, such as that disclosed in commonly assigned U.S. patent application Ser. No. 10/372,032 (the entirety of which is incorporated herein by this reference and is now publicly available as U.S. Patent Application Publication No. 20030198576), may be incorporated in or otherwise in fluid communication with the microfluidic HPLC device. An HPLC separation is then performed on the incubated solution. A control standard of pure enzyme may be separated on one HPLC column. If the target molecule interacts with the enzyme and is bound, the position of the enzyme peak on the chromatogram obtained from the sample HPLC column will move relative to the peaks appearing in the chromatogram obtained from the control column. Likewise, if the target molecule cleaves the enzyme, multiple peaks will show up on the chromatogram. Because most proteins and peptides contain molecular moieties that absorb UV light, no tagging of the enzymes is necessary. Thus, assay development may be minimized or eliminated entirely, thus enhancing analytical throughput.

Of course, multiple sample preparation steps may be combined for more complex processes. For example, many protein analyses include an extraction step followed by a degradation step (where large proteins are broken down into smaller peptides that are then analyzed using HPLC). The degraded protein sample also may be filtered or otherwise purified prior to performing a separation. Other useful processes include, without limitation, protein precipitation, cell fractionation, solvent extraction, and desalting. It will be readily apparent to one of ordinary skill in the art that any of the microfluidic sample preparation structures described above, as well as other useful microfluidic sample preparation structures may be combined to perform any number of desirable sample preparation processes.

In addition, sample preparation steps may be performed in a separate microfluidic device that is physically distinct from a multi-column separation device, as shown in FIGS. 10A–16. A number of benefits arise by the use of separate sample preparation and separation devices. For example, different sample preparation processes may be selected through the use of various sample preparation devices without requiring a change in the separation columns in use. Also, sample preparation devices may become fouled by contaminants; thus, a separate, disposable sample preparation device can simplify operation of the HPLC system. Furthermore, the sample preparation device may be adapted to permit parallel preparation of sample sets, further reducing the cycle time of the HPLC system.

Referring to FIGS. 10A–10C, one example of a stand-alone sample preparation device 700 comprises multiple sample preparation elements 702A–702X. Each sample preparation element 702A–702X includes a sample inlet 704A–704X, a mobile phase inlet 706A–706X, and a mobile phase outlet 708A–708X. One or more membranes 710, 712 may be provided. The device 700 is fabricated from six device layers 701A–701F.

FIG. 11 illustrates the sample injection section of a HPLC device 720 similar to that illustrated in FIG. 1A (although only one separation column is shown, it should be understood that FIG. 11 illustrates, for simplicity, a cross section of one sample injection section of one column in a multi-column device). The HPLC device 720 includes a mobile phase outlet 722A, a mobile phase/sample inlet 724A, a mobile phase manifold 726, a frit 728, a separation column 730A, and stationary phase packing manifold 732. Stationary phase material (not shown) for performing liquid chromatography is packed into the separation column 730A via the packing manifold 732. The solid phase material is retained within the column 730A by the frit 728.

FIG. 12 illustrates the interface 740 between the stand-alone sample preparation device 700 and the sample injection section of the HPLC device 720. The interface 740 includes a mobile phase conduit 744A and a mobile phase/sample conduit 742A. The interface 740 may be fabricated from any suitable material, preferably a chemically inert or non-contaminating material including, but not limited to, stainless steel, polyimide, polypropylene, a fluoropolymer, or glass. The interface 740 is preferably at least partially planar to ensure a pressure-tight seal between the interface 740 and the sample preparation device 700 and the HPLC device 720.

In operation, the sample preparation device 700 is positioned against the interface 740 so that the mobile phase inlet 708A is aligned with the mobile phase conduit 744A and the mobile phase/sample outlet 706A is aligned with the mobile phase/sample conduit 742A. A seal is formed between the devices 700, 740 by gaskets 746A, 747A, or other suitable sealing mechanisms, such as gasketless pressure seals. Notably, a press-fit may be used to establish a desired seal without the use of threaded fittings. A pressure plate or similar compression element (not shown) may be positioned above and compressed against the sample preparation device 700, thereby sandwiching the sample preparation device 700 and the interface 740 to maintain the desired seal. The HPLC device 720 is positioned against the interface 740 so that the mobile phase outlet 722A is aligned with the mobile phase conduit 744A and the mobile phase/sample inlet 724A is aligned with the mobile phase/sample conduit 742A. A (preferably threadless) seal is formed between the devices 720, 740 by gaskets 748A, 749A, or other suitable sealing mechanisms. A pressure plate or similar support surface as part of a compression element (not shown) may be positioned below and compressed against the HPLC device 720, thereby sandwiching the HPLC device 720 and the interface 740 to maintain the desired seal.

Once the devices 700, 720 are mated with the interface 740, a sample (not shown) is deposited in the sample inlet 704A by manual or automated means. The sample inlet is then sealed with a sealing plate 750 and a mobile phase is pumped through the mobile phase manifold 726 through the mobile phase outlet 722 and into the mobile phase conduit 744A. The mobile phase then enters the sample preparation device 700 through the mobile phase inlet 708A and passed through the first membrane 710. The mobile phase entrains the sample and carries it through the sample preparation element 702A and the membrane 712. The mobile phase/sample combination then travels through the mobile phase/sample outlet 706A and into the mobile phase/sample conduit 742. The mobile phase/sample combination then enters the HPLC device 720 through the mobile phase/sample inlet 724A and enters the column 730A where the separation is performed.

Various types of sample preparation methods may be performed. For example, the sample processing element 702A may include reagents or diluents to act as a reaction vessel to create reaction analytes, precipitate proteins, or desalt the sample; the membrane 706A may be a size exclusion or chemical affinity filter to purify the sample; or any combination thereof. Moreover, it will be readily apparent to one skilled in the art that the structure may be modified to include mechanisms for performing any of the sample preparation processes described above. In addition, the sample preparation device 700 could be mated directly to the HPLC device 720, obviating the need for a separate interface 740. Also, the mobile phase conduit 744 and the mobile phase/sample conduit 742 may be vias defined in the interface 740 as illustrated or any other suitable mechanism for transferring fluids, such as capillary conduits.

As illustrated in FIG. 13, a sequential parallel sample preparation device 800 may include multiple sample preparation sets 801A–801X, each set including multiple parallel sample preparation elements 802A–802X (for simplicity only the sample preparation elements of sample separation set 801B are numbered). The term "sequential parallel" refers to a device adapted to utilize (preferably only once) a first set of parallel sample preparation elements for a first parallel sample preparation run, and then utilize (preferably only once) a second set of parallel sample preparation elements for a second parallel sample separation run, and so on. The number of sample preparation elements 802A–802X contained in a single sequential parallel sample preparation device 800 should significantly exceed the number of separation columns in an associated multi-column separation device. As described above with respect to FIGS. 10A–10C, each sample preparation element 802A–802X preferably includes a mobile phase inlet 806A–806X, a sample inlet 804A–804X, and a mobile phase/sample outlet 808A–808X. Each sample preparation set 801A–801X may include one or more membranes 810A–810X, 812A–812X. The sample preparation elements 802A–802X may be configured for any desired sample preparation process, as discussed above.

In operation, the sequential parallel sample preparation device 800 may be used in the same manner as shown in FIG. 12. This approach provides the ability to periodically advance (e.g., translate or otherwise move) the sequential parallel sample preparation device 800 across the interface 740 using an automated or manual translation system, which, in turn, reduce the frequency at which the sequential parallel sample preparation device 800 must be replaced.

In another example, shown in FIG. 14, a sequential parallel sample preparation device 800 may be used to reduce the cycle time associated with performing separations on (e.g., analyzing) multiple sets of samples. A two stage interface 840 is provide, which includes all of the features described above with respect to interface 740 as well as a sample preparation stage including first and second fluid conduits 860A, 870A. When a sequential parallel sample preparation device 800 is mated to the interface 840, a sample separation set 801B is placed in fluid communication with the first and second fluid conduits 860A, 870A—specifically, the mobile phase inlet 806A of the sample preparation element 802A is mated to one fluid conduit 870A and sealed with a gasket 853A, O-ring, gasketless surface contact, or other appropriate and preferably threadless sealing means. The mobile phase/sample outlet 808A of the sample preparation element 802A is mated to one fluid conduit 860A and sealed with a gasket 852A or other appropriate sealing means. Once a seal is formed between the sequential parallel sample preparation device 800 and the interface 840, a sample may be introduced into the sample inlet 804A and sealed in with a sealing plate 851 or other appropriate sealing mechanism. The sample may then be prepared by introducing and removing fluids through the fluid conduits 860A, 870A. For example, the membranes 810B, 812B have a chemical affinity for the sample being prepared when dissolved fluids having particular characteristics. Such a fluid may be pumped through the sample preparation element 802A to bind the sample to the membranes 810A, 812A while washing away impurities. Of course, the number and arrangement of fluid conduits 860A, 870A, may be varied as necessary to perform the desired sample preparation—i.e., the sample preparation elements 802A–802X and the interface may be modified to perform any of the sample preparation processes described above, as well as other useful sample preparation processes.

While one sample preparation set 802B is mated to the interface 840, other sample preparation sets 801A, 801C–801X may also be mated to the interface. For example, as illustrated in FIG. 14, a first sample preparation set 801A is mated to an HPLC device 820 via the interface 840. Thus, while samples are being prepared in a second sample preparation set 801B, samples in the first sample preparation set 801A may be separated and analyzed. Moreover, the sequential parallel sample preparation device 800 may be translated, whether manually or automatically with appropriate automation element(s), to travel across the interface 840. In this manner, samples in first sample set 801A are transferred to the HPLC device 820 for separation while samples in a second sample preparation set 801B a substantially simultaneously prepared for separation. Once both operations are complete, the sequential parallel sample preparation device 800 is translated so that the second sample separation set 801B is mated to the HPLC device 820 and a third sample separation set 801C is prepared. Because separation steps and sample preparation steps may occur substantially simultaneously, cycle times for running successive sample sets may be reduced. Moreover, multiple sample preparation stages may be provided on the interface 840 to permit more complex and multi-step sample preparation processes to be used.

FIG. 15 illustrates a high throughput analytical system 900 according to the invention. The system 900 comprises a sample delivery subsystem 901, a sample preparation subsystem 902, a chromatographic subsystem 903, and a detection subsystem 904.

The sample delivery subsystem 901 comprises a sample source 905 and one or more transfer elements 906A–906X. The sample source 905 may be any desirable sample storage and retrieval system or format, such as well-plates or microwell plates. The transfer elements 906A–906X may be any suitable mechanism for transferring the samples from the sample source 905 to the sample preparation subsystem 902. Examples of suitable transfer elements include manual pipettors, automated pipettors, robotic samplers, and capillary lines.

The sample preparation subsystem 902 comprises a sample preparation device 907, an upper seal plate 908, a lower seal plate 909, a compression element 910, a waste receptacle 911, a translation element 912 and one or more common fluid supplies 913, 914.

The sample preparation device 907 may selected from any of the sample preparation device types or configurations discussed above in any desired combination.

The upper seal plate 908 and a lower seal plate 909 are substantially planar plates adapted to engage and form a seal with the sample preparation device 907. The upper seal plate 908 and a lower seal plate 909 may be fabricated from any suitable material, including include, but not limited to: fluoropolymers, poly(ether ether ketone) (PEEK), polyimide, stainless steel, or any other material having sufficient structural characteristics and a chemically compatible make-up or coating. Optionally, the upper seal plate 908 and a lower seal plate 909 may include gaskets 908A, 909A or other suitable sealants to ensure an appropriate seal between the upper seal plate 908 and a lower seal plate 909 and the sample preparation device 907. The upper seal plate 908 and a lower seal plate 909 preferably include one or more orifices or ports (not shown) adapted to permit fluids to enter and exit the sample preparation device as required to perform the desired sample preparation processes.

The compression element 910 engages the upper seal plate 908 and lower seal plate 909 to compress them against the sample preparation device 907. The compression element 910 may include any suitable actuator, including, but not limited to, hydraulic pistons, electromechanical actuators, screw-type actuators, or manually actuated clamps.

The waste receptacle 911 may include any container suitable for capturing fluids exiting the sample preparation device 907 for disposal, including, but not limited to, laboratory fluid containers, buckets, hazardous material disposal containers, and drains to sewage.

The translation element 912 may include any suitable mechanism for translating the sample preparation device as required to operate the system 900. For example, the translation element 912 may be adapted to periodically translated the sample preparation device 907 in predetermined steps to allow the use of sequential parallel sample preparation devices discussed above. Alternatively (or additionally), the translation element 912 may be adapted to remove and replace the sample preparation device 907 after each cycle.

The common fluid supplies 913, 914 may be any systems for supplying fluids as required to operate the sample preparation device 907. Suitable systems include, but are not limited to, laboratory reservoirs containing the desired solvents and other fluids used in sample preparation and pumps or vacuum systems for moving the fluids into and out of the sample preparation device 907.

The chromatographic separation subsystem comprises multiple sample delivery conduits 920A–920X, a liquid chromatography device 930, an upper seal plate 931, a lower seal plate 932, a compression element 933, and one or more common fluid supplies 934, 935.

The multiple sample delivery conduits 920A–920X may be any suitable means for transferring samples from the sample preparation device 907, including, but not limited to, capillary lines or interfaces such as that described above with reference to FIGS. 12 and 14.

The liquid chromatography device 930 may include any device adapted to perform multiple simultaneous chromatographic separations. Suitable devices include the multi-column devices described above, the Veloce™ micro-parallel liquid chromatography system utilizing Brio™ cartridges (Nanostream, Inc., Pasadena, Calif.), or multiple ganged convention HPLC columns.

The upper seal plate 931 and lower seal plate 932 preferably include substantially planar plates adapted to engage and form a seal with the liquid chromatography device 930. The upper seal plate 931 and a lower seal plate 932 may be fabricated from any suitable material, including include, but not limited to: fluoropolymers, poly(ether ether ketone) (PEEK), polyimide, stainless steel, or any other material having sufficient structural characteristics and a chemically compatible make-up or coating. Optionally, the upper seal plate 931 and a lower seal plate 932 may include gaskets 931A, 932A or other suitable sealing elements to ensure an appropriate seal between the upper seal plate 931 and a lower seal plate 931 and the liquid chromatography device 930. The upper seal plate 931 and a lower seal plate 932 may include one or more orifices or ports (not shown) adapted to permit fluids to enter and exit the liquid chromatography device 930 as required to perform the desired chromatographic separation processes.

The compression element 933 engages the upper seal plate 931 and lower seal plate 932 to compress them against the liquid chromatography device 930 and may include any suitable actuator, including, but not limited to, hydraulic pistons, electromechanical actuators, —type actuators, or manually actuated clamps.

The common fluid supplies 934, 935 may include any systems for supplying fluids as required to operate the liquid chromatography device 930. Suitable systems include, but are not limited to, laboratory reservoirs containing the desired solvents and other fluids used in sample preparation and pumps or vacuum systems for moving the fluids into and out of the liquid chromatography device 930.

The detection subsystem 904 may comprise a flow-through detection instrument 940 and a consumptive detection instrument 941. The flow-through detection instrument 940 may perform any suitable form of detection and analysis, including, but not limited to, UV-visible spectroscopy, Raman spectroscopy, fluorescence detection, chemiluminescence, electrochemical detection, capacitive measurement, and conductivity measurement. The consumptive detection instrument 941, if provided, may perform any suitable form of detection and analysis, including, but not limited to, mass spectrometry, nuclear magnetic resonance, evaporative light scattering, ion mobility spectrometry, and matrix-assisted laser desorption ionization (MALDI). Of course, any combination of one or more of each form of detection may be used to obtain the desired measurements.

In operation, the sample preparation device 907 is secured between the upper and lower seal plates 907, 908 and compressed by the compression element 910 and the liquid chromatography device 930 is secured between the upper and lower seal plates 931, 932 and compressed by the compression element 933. Samples (not shown) are selected from the sample source 905 and delivered to the sample preparation device 907 via the transfer elements 906A–906X. The samples are then prepared in the sample preparation device 907 using the desired sample preparation process (e.g., using one of the sample preparation processes described herein). Any fluids used in the sample preparation process are provided by the common fluid supplies 913, 914. Following processing within the sample preparation device 907, the prepared samples are delivered to the liquid chromatography device 930 via the sample delivery conduits 920A–920X. The sample preparation device 907 may be re-used or discarded. If the sample preparation device 907 is a sequential-parallel device, then the translation element 912 may be used to reposition the sample preparation device 907 as desired to permit continued operation using a fresh set of parallel sample preparation elements. If the sample preparation device 907 is disposable, the translation element 912 may be used to remove and discard the sample preparation device 907.

The prepared samples are processed by the liquid chromatography device 930 in a desired manner (e.g., isocratic separation, gradient separation, or other suitable separation techniques may be used). The mobile phase used to perform the separation is provided by the common fluid supplies 934, 935. The eluate from each separation column of the multi-column chromatography device 930 is then analyzed using the flow-through detection instrument 940 and/or consumptive detection instrument 941.

In another embodiment as depicted in FIG. 16, a sample preparation subsystem 1000 comprises a sample preparation device 1001, an upper seal plate 1002, a lower seal plate 1003, a compression element 1004, a collection/waste receptacle 1005, a translation element 1006A–1006B, and one or more transport subsystems 1007A–1007C, 1008.

The sample preparation device 1001 may include sample preparation elements (not shown) selected from any of the sample preparation devices described herein in any desired combination. Moreover, as depicted in FIG. 16, the sample preparation device 1001 may be provided as a continuous strip or roll containing multiple sets of sample preparation elements.

The upper seal plate 1002 and a lower seal plate 1003 preferably include substantially planar plates adapted to engage and form a seal with at least a potion of the sample preparation device 1001. The upper seal plate 1002 and lower seal plate 100 may be fabricated from any suitable material, including include, but not limited to: fluoropolymers, poly(ether ether ketone) (PEEK), polyimide, stainless steel, or any other material having sufficient structural characteristics and a chemically compatible make-up or coating. Optionally, the upper seal plate 1002 and a lower seal plate 1002 may include gaskets 1002A, 1003A, O-rings, gasketless interconnects, or other suitable sealing means to ensure an appropriate seal between the upper seal plate 1002 and a lower seal plate 1003 and the sample preparation device 1001. The upper seal plate 1002 and a lower seal plate 1003 may include one or more orifices or ports (not shown) adapted to permit fluids to enter and exit the sample preparation device 1001 as required to perform the desired sample preparation processes.

The compression element 1004 engages the upper seal plate 1002 and a lower seal plate 1003 to compress them against the sample preparation device 1001 and may be any suitable actuator, including, but not limited to, hydraulic pistons, electromechanical actuators, screw-type actuators, or manually actuated clamps.

The collection/waste receptacle 1005 may be any container suitable for capturing fluids exiting the sample preparation device 1001 for further analysis and/or disposal, including, but not limited to, fraction collectors, laboratory fluid containers, buckets, hazardous material disposal containers, and drains to sewage.

The translation element 1006A–1006B may be a spooling mechanism (e.g., utilizing feed and take-up rollers coupled to a stepper motor (not shown)) for moving a continuous roll of the sample preparation device 1001. For example, translation element 1006A–1006B may be adapted to periodically translate the sample preparation device 1001 in predetermined steps to allow the use of sequential parallel sample preparation devices discussed above.

The transport subsystems 1007A–1007C, 1008 may include one or more mechanisms for driving fluids through or within the sample preparation device 1001 in order to effect the desired preparation process. For example, certain assay processes require the use of a vacuum to draw a sample through a porous membrane (allowing analysis of either the filtrate or retentate). Thus, the transport subsystem may include a vacuum source 1008 to provide the requisite vacuum to the sample preparation device 1001. Similarly, it may be desirable to perform on the sample some form of electrokinetic process, such as electrophoresis. Thus, the transport subsystem may include an electrokinetic system comprising voltage sources and sinks 12007A, 1007C and a transport fluid source 1007B. One or more electrodes 1007D may protrude from the upper or lower seal plates 1002, 1003 and interface with the sample preparation device 1001 to provide the electrical signal required to implement the electrokinetic flow. Moreover, electrical conduits or pathways (not shown) may be provided within the sample preparation device 1001 to further facilitate electrokinetic operations.

In operation, samples (not shown) are transferred from the sample source 1010 to the sample preparation device 1001. The samples are processed in the sample preparation device 1001 in the selected manner (e.g., vacuum filtration, electrokinetic based process) and delivered to an HPLC device (not shown) in the manner described above with respect to FIG. 15.

As noted previously, sample preparation devices may be adapted to perform quantitative or qualitative tests such as assays. Examples of desirable assays include permeability assays (e.g., phospholipid artificial membrane permeability assay or "PAMPA"); solubility assays (e.g., utilizing silica-based separation media to which carbon chains (e.g., C2, C6, or C18) have been added for ascertaining the relative solubility of different analytes in a given solvent environment); bioaffinity assays (e.g., utilizing specific binding media adapted to bind selected types of molecules); and sandwich assays (e.g., utilizing an array of labeled captured ligands as antibodies pre-bound with labeled receptors or antigens to look for various analytes to compete off of the labeled receptors or antigens).

Permeability assays are often designed to predict passive, transcellular permeability of drugs. An artificial membrane disposed between a donor region and an acceptor region is used to measure the ability of compounds to diffuse from the donor region to the acceptor region. Vacuum may be used to draw samples through the membrane. One type of permeability assay is the Parallel Artificial Membrane Permeation Assay (PAMPA), as introduced by Kansy, et al. (see, e.g., Kansy M, Senner F, Gubernator K., "Physicochemical high throughput screening: parallel artificial membrane permeation assay in the description of passive absorption processes," J Med Chem 1998;41:1007–1010). The pH of solutions used in the analysis can be adjusted to determine the effect of pH on compound permeability. Various types of membranes that can be used for permeability assays include a polycarbonate support (e.g., 3 µm track etched, 10 µm thickness) with a hexadecane artificial membrane, and a PVDF support (e.g., 0.45 µm) with a lecithin in dodecane artificial membrane.

Solubility assays are typically used to determine compound solubility in water. A traditional solubility assay method utilizes a shake flask and involves adding an excess quantity of solid material to a volume of buffer at a set pH. Since shake-flask solubility methods are inherently low throughput, filtration-based assays have been developed. A conventional device for performing solubility assays is the Millipore MultiScreen Solubility plate, catalog no. MS SLB PC 10 (Millipore Corp., Billerica, Mass.), utilizing a 0.4 µm modified PCTE membrane. Buffers and samples are dispensed into well plates having solubility membranes, and then covered and shaken. Filtration may be accomplished by vacuum, and then an appropriate method such as UV spectroscopy may be used to quantify dissolved compound versus standard curves.

Various affinity media suitable for bioaffinity assays and/or purification of tagged proteins, monoclonal and polyclonal antibodies, glycoproteins, enzymes, nucleic acids, cells, and other proteins are commercially available, e.g., from Amersham Biosciences (Piscataway, N.J.) and Millipore Corp. (Billerica, Mass.).

A schematic illustration of reagents and products of a parallel sandwich-type (affinity) assay is provided in FIG. 17. An array is provided of multiple analytical regions or wells containing the same type of ligand or antibody (represented schematically as a "circle-Y" combination in FIG. 17) to which a labeled receptor mimic or antigen mimic (e.g., the mimic and tag are represented by "D*" in FIG. 17) is bound—preferably weakly. Preferred label types are fluorescent tags to permit fluorescent detection of the mimics. A different analyte-containing sample (e.g., A, B, C) is then supplied to each analytical region or well. If the analyte (e.g., A, B, C) has any affinity for the ligand or antibody, then it may compete off and ultimately displace the receptor/antigen mimic (e.g., D*). The relative amounts of unbound (free) analyte (e.g., A, B, C) and receptor/antigen mimic (e.g., D") that results in each analytical region or well may be measured to determine the relative affinity of the analytes (e.g., A, B, C) for the ligands/antibodies. In the example shown in FIG. 17, the analyte A contained in the first analytical region has a greater affinity for the ligand/antibody than the mimic D*, thus displacing D* from the and resulting in a relatively high concentration of unbound D* in the analytical region. Parallel liquid chromatography and an appropriate detection technique may then be used to analyze the unbound contents of the "prepared" samples to determine presence of and/or quantify the unbound free contents. Preferably, the ratios of the labeled mimic to the analyte initially supplied to each analytical region are compared to determine relative affinity for the ligands/antibodies.

Figure 18:
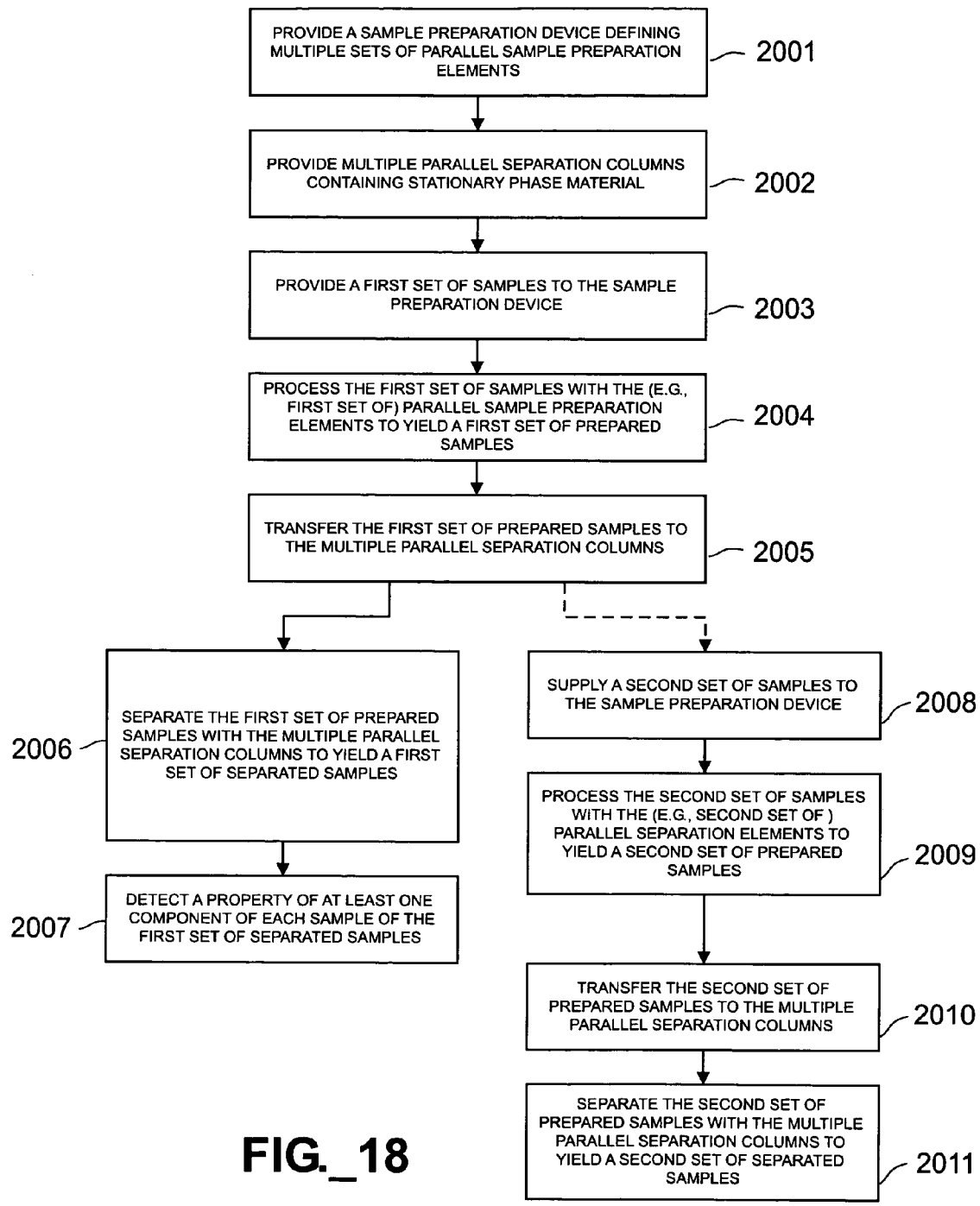
FIG. 18 is a flowchart showing various steps of a parallel fluid processing method including sample preparation and chromatographic separation steps.

Referring to FIG. 18, a method for preparing and analyzing multiple sets of samples includes multiple method steps. A first step 2001 includes providing a sample preparation device defining multiple sets of parallel sample preparation elements. A second step 2002 includes providing multiple parallel separation columns containing stationary phase material. A third step 2003 includes providing a first set of samples to the sample preparation device. A fourth step 2004 includes processing the first set of samples with the (e.g., first set of) parallel sample preparation elements to yield a first set of prepared samples. A fifth step 2005 includes transferring the first set of prepared samples to the multiple of parallel separation columns. A sixth step 2006 includes separating the first set of prepared samples with the plurality of sets of parallel separation columns. A seventh step 2007 includes detecting a property of at least one component of each sample of the first set of separated samples. An eighth step 2008 includes supplying a second set of samples to the sample preparation device. A ninth step 2009 includes processing the second set of samples with the (e.g., second set of) parallel sample preparation elements to yield a second set of prepared samples. A tenth step 2010 includes transferring the second set of prepared samples to the multiple of parallel separation columns. An eleventh step 2011 includes separating the second set of prepared samples with the plurality of sets of parallel separation columns. Notably, certain steps may be performed substantially simultaneously. For example, the ninth step 2009 may be performed substantially simultaneously with the sixth step 2006 and the seventh step 2007. One significant advantage of this capability is to reduce overall cycle time associated with processing and separating multiple sets of samples.

Thus, various inventive systems and elements thereof have been described herein. It is also to be appreciated that the foregoing description of the invention has been presented for purposes of illustration and explanation and is not intended to limit the invention to the precise manner of practice herein. It is to be appreciated therefore, that changes may be made by those skilled in the art without departing from the spirit of the invention.

What is claimed is:

1. A microfluidic parallel fluid processing system comprising:
   a plurality of parallel separation columns containing stationary phase material;
   a sample preparation device defining a plurality of parallel sample preparation elements and a plurality of sample outlet ports in fluid communication with the plurality of sample preparation elements;
   a first fluid supply; and
   an interface adapted to threadlessly engage at least a portion of the sample preparation device to establish temporary fluid communication between the first fluid supply, at least some sample preparation elements of the plurality of sample preparation elements, and the plurality of separation columns.

2. The system of claim 1 wherein the plurality of sample outlet ports is in fluid communication with the plurality of separation columns.

3. The system of claim 1, further comprising a plurality of fluid conduits disposed between the plurality of sample outlet ports and the plurality of separation columns.

4. The system of claim 1 wherein at least a portion of the interface is moveable.

5. The system of claim 1 wherein the at least a portion of the interface is substantially planar.

6. The system of claim 1 wherein the interface comprises a gasket.

7. The system of claim 1 wherein the interface comprises:
   a first interface portion between the first fluid supply and the sample preparation device; and
   a second interface portion between the sample preparation device and the plurality of separation columns.

8. The system of claim 1 wherein the first fluid supply comprises a pump and a reservoir.

9. The system of claim 1 further comprising a second fluid supply.

10. The system of claim 1 further comprising a vacuum source in fluid communication with the plurality of sample preparation elements.

11. The system of claim 1 further comprising a voltage source in electrical communication with the plurality of sample preparation elements.

12. The system of claim 1 further comprising a translation element adapted to move the sample preparation device relative to the interface.

13. The system of claim 1 wherein the number of sample preparation elements of the plurality of sample preparation elements exceeds the number of separation columns of the plurality of separation columns.

14. The system of claim 1 wherein each of the plurality of separation columns and the sample preparation device is integrated within a unitary body structure.

15. The system of claim 1 further comprising a plurality of sample injectors adapted to intermittently supply a plurality of samples to a plurality of sample inlet ports.

16. The system of claim 1 wherein each sample preparation element of the plurality of sample preparation elements comprises packed particulate material.

17. The system of claim 1 wherein each sample preparation element of the plurality of sample preparation elements comprises a porous membrane.

18. The system of claim 1 wherein each sample preparation element of the plurality of sample preparation elements comprises a guard column.

19. The system of claim 1 wherein the plurality of sample preparation elements is adapted to perform any of: size exclusion filtration, chemical affinity filtration, solid phase extraction, liquid phase extraction, protein precipitation, and desalting.

20. The system of claim 1 wherein the plurality of sample preparation elements is adapted to perform any of serial dilution and metering.

21. The system of claim 1 wherein the plurality of sample preparation elements is adapted to perform any of: permeability assays, solubility assays, bioaffinity assays, sandwich assays, and enzymatic assays.

22. The system of claim 1, further comprising a flow-through detector.

23. The system of claim 22 wherein the flow-through detector is adapted to perform any of: UV-visible spectroscopy, Raman spectroscopy, fluorescence detection, chemiluminescence, electrochemical detection, capacitive measurement, and conductivity measurement.

24. The system of claim 1, further comprising a consumptive detector.

25. The system of claim 24 wherein the flow-through detector is adapted to perform any of: mass spectrometry, nuclear magnetic resonance, evaporative light scattering, ion mobility spectrometry, and matrix-assisted laser desorption ionization.

* * * * *

UNITED STATES PATENT AND TRADEMARK OFFICE
CERTIFICATE OF CORRECTION

PATENT NO. : 7,074,327 B2
APPLICATION NO. : 10/841242
DATED : July 11, 2006
INVENTOR(S) : Steven D. O'Connor et al.

It is certified that error appears in the above-identified patent and that said Letters Patent is hereby corrected as shown below:

On the title page, item [56.]:
In the References Cited: Other Publication section, page 2, first column, "Fang, Liling et al., *High-throughput liquid chromatograpohy Ultraviolet.mass spectrometric analysis of combinatorial libraries using an eight-channel multiplexed electrospray time-of-flight mass spectrometer*, "Rapid Communications in Mass Spectrometry," 2002; 16:1440-1447" should be -- Fang, Liling et al., *High-throughput liquid chromatograpraphy Ultraviolet/mass spectrometric analysis of combinatorial libraries using an eight-channel multiplexed electrospray time-of-flight mass spectrometer*, "Rapid Communications in Mass Spectrometry," 2002; 16:1440-1447 --

In the References Cited: Other Publications section, page 2, second column, "Berna, M. et al., *Collection Storage and Filtration of in Vivo Study Samples Using 96-Well Filter Plates to Facilitate Automated Sample Preparation and LC/MS.MS Analysis*, "Analytical Chemistry," vol. 74, No. 5, Mar. 1, 2002, pp. 1197-1201" should be -- Berna, M. et al., *Collection, Storage and Filtration of in Vivo Study Samples Using 96-Well Filter Plates to Facelitate Automated Sample Preparation and LC/MS/MS Analysis*, "Analytical Chemistry," vol. 74, No. 5, Mar. 1, 2002, pp. 1197-1201 --

In the References Cited: Other Publications section, page 2, second column, "Taylor, M.T. et al., "Fully Automated Sample Preparation for Pathogen Detection Performed in a Microfludic Cassette," *Micro Total Analysis Systems,* J.M. Ramsey and A. van den Berg (eds.), 2001, pp. 670-672, Kluwer Academic Publishers, The Netherlands" should be
-- Taylor, M.T. et al., "Fully Automated Sample Preparation for Pathogen Detection Performed in a Microfluidic Cassette," *Micro Total Analysis Systems,* J.M. Ramsey and A. van den Berg (eds.), 2001, pp. 670-672, Kluwer Academic Publishers, The Netherlands --

In the Refernces Cited: Other Publications section, page 3, first column, fourth line, "Kluwer Acedemic Publishers" should be -- Kluwer Academic Publishers --

UNITED STATES PATENT AND TRADEMARK OFFICE
CERTIFICATE OF CORRECTION

PATENT NO. : 7,074,327 B2
APPLICATION NO. : 10/841242
DATED : July 11, 2006
INVENTOR(S) : Steven D. O'Connor et al.

It is certified that error appears in the above-identified patent and that said Letters Patent is hereby corrected as shown below:

Column 8, line 50: "packing 50" should be -- packing manifold 50 --

Signed and Sealed this

Fourteenth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,074,327 B2
APPLICATION NO. : 10/841242
DATED : July 11, 2006
INVENTOR(S) : Steven D. O'Connor et al.

It is certified that error appears in the above-identified patent and that said Letters Patent is hereby corrected as shown below:

On the title page, item [56.]:
In the References Cited: Other Publication section, page 2, first column, "Fang, Liling et al., *High-throughput liquid chromatograpohy Ultraviolet.mass spectrometric analysis of combinatorial libraries using an eight-channel multiplexed electrospray time-of-flight mass spectrometer*, "Rapid Communications in Mass Spectrometry," 2002; 16:1440-1447" should be -- Fang, Liling et al., *High-throughput liquid chromatography Ultraviolet/mass spectrometric analysis of combinatorial libraries using an eight-channel multiplexed electrospray time-of-flight mass spectrometer*, "Rapid Communications in Mass Spectrometry," 2002; 16:1440-1447 --

In the References Cited: Other Publications section, page 2, second column, "Berna, M. et al., *Collection Storage and Filtration of in Vivo Study Samples Using 96-Well Filter Plates to Facilitate Automated Sample Preparation and LC/MS.MS Analysis*, "Analytical Chemistry," vol. 74, No. 5, Mar. 1, 2002, pp. 1197-1201" should be -- Berna, M. et al., *Collection, Storage and Filtration of in Vivo Study Samples Using 96-Well Filter Plates to Facilitate Automated Sample Preparation and LC/MS/MS Analysis*, "Analytical Chemistry," vol. 74, No. 5, Mar. 1, 2002, pp. 1197-1201 --

In the References Cited: Other Publications section, page 2, second column, "Taylor, M.T. et al., "Fully Automated Sample Preparation for Pathogen Detection Performed in a Microfludic Cassette," *Micro Total Analysis Systems,* J.M. Ramsey and A. van den Berg (eds.), 2001, pp. 670-672, Kluwer Academic Publishers, The Netherlands" should be
-- Taylor, M.T. et al., "Fully Automated Sample Preparation for Pathogen Detection Performed in a Microfluidic Cassette," *Micro Total Analysis Systems,* J.M. Ramsey and A. van den Berg (eds.), 2001, pp. 670-672, Kluwer Academic Publishers, The Netherlands --

In the Refernces Cited: Other Publications section, page 3, first column, fourth line, "Kluwer Acedemic Publishers" should be -- Kluwer Academic Publishers --

UNITED STATES PATENT AND TRADEMARK OFFICE
CERTIFICATE OF CORRECTION

PATENT NO. : 7,074,327 B2
APPLICATION NO. : 10/841242
DATED : July 11, 2006
INVENTOR(S) : Steven D. O'Connor et al.

It is certified that error appears in the above-identified patent and that said Letters Patent is hereby corrected as shown below:

Column 8, line 50: "packing 50" should be -- packing manifold 50 --

This certificate supersedes Certificate of Correction issued November 14, 2006.

Signed and Sealed this

Seventeenth Day of April, 2007

JON W. DUDAS
*Director of the United States Patent and Trademark Office*